(12) United States Patent
Heidelbaugh et al.

(10) Patent No.: US 7,838,545 B2
(45) Date of Patent: Nov. 23, 2010

(54) 4-(CONDENSED CYCLICMETHYL)-IMIDAZOLE-2-THIONES ACTING AS ALPHA2 ADRENERGIC AGONISTS

(75) Inventors: Todd M. Heidelbaugh, Fountain Valley, CA (US); Ken Chow, Newport Coast, CA (US); Phong X. Nguyen, Placentia, CA (US); Daniel W. Gill, Corona Del Mar, CA (US); John E. Donello, Dana Point, CA (US); Michael E. Garst, Newport Beach, CA (US); Larry A. Wheeler, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 4 days.

(21) Appl. No.: 12/166,964

(22) Filed: Jul. 2, 2008

(65) Prior Publication Data

US 2009/0176828 A1 Jul. 9, 2009

Related U.S. Application Data

(63) Continuation of application No. 11/232,383, filed on Sep. 20, 2005, now Pat. No. 7,396,849.

(60) Provisional application No. 60/612,939, filed on Sep. 24, 2004.

(51) Int. Cl.
  *A61K 31/4174* (2006.01)
  *C07D 233/42* (2006.01)
(52) U.S. Cl. .................. 514/386; 548/311.4; 548/316.4
(58) Field of Classification Search .................. 514/386; 548/311.4, 316.4
  See application file for complete search history.

(56) References Cited

U.S. PATENT DOCUMENTS

| 4,798,843 | A | 1/1989 | Kruse | |
|---|---|---|---|---|
| 6,124,300 | A | 9/2000 | Rajagopalos | |
| 6,486,187 | B1 | 11/2002 | Venet | |
| 6,534,542 | B2 * | 3/2003 | Chow et al. | 514/546 |
| 7,091,232 | B2 | 8/2006 | Chow et al. | |
| 7,141,579 | B2 | 11/2006 | Kawashima et al. | |
| 7,312,238 | B2 | 12/2007 | Chow et al. | |
| 7,323,485 | B2 | 1/2008 | Chow et al. | |
| 7,396,849 | B2 * | 7/2008 | Heidelbaugh et al. | 514/386 |

FOREIGN PATENT DOCUMENTS

| EP | 030-2603 | 2/1989 |
|---|---|---|
| GB | 1499485 | 2/1979 |
| JP | 06067368 | 3/1994 |
| JP | 2002097310 | 4/2002 |
| JP | 2002097312 | 4/2002 |
| WO | WO 99/28200 | 6/1999 |
| WO | WO 99/28300 | 6/1999 |
| WO | WO 01/00586 | 1/2001 |
| WO | WO 02/36162 | 5/2002 |
| WO | WO 03/099795 | 12/2003 |
| WO | WO 2005/034849 | 4/2005 |
| WO | WO 2005-034946 | 4/2005 |

OTHER PUBLICATIONS

Ruffolo, Jr., "α-*Adrenoreceptors*": *Molecular Biology, Biochemistry and Pharmacology*, (Progress in Basic and Clinical Pharmacology series, Karger, 1991).

Messier et al, High Throughput Assays of Cloned Adrenergic, Muscarinic, Neurokinin, and Neurotrophin Receptors in Living Mammalian Cells, 1995, 76, pp. 308-311.

Conklin et al, "Substitution of three amino acids switches receptor specificity of Gqα to that of G1α", 1993, Nature 363: 274-6.

Dirig et al, "Characterization of variables defining hindpaw withdrawal latency evoked by radiant thermal stimuli",J. Neurosci. Methods, 1997, 76: 183-191.

Hargreaves et al, "A new and sensitive method for measuring thermal nociception in cutaneous hyperalgesia", 1988, Pain 32: 77-88.

Dixon, W.J., "Efficient Analysis of Experimental Observations", Ann. Rev. Pharmacol. Toxicol., 1980, 20: 441-462.

(Continued)

*Primary Examiner*—Joseph K. McKane
*Assistant Examiner*—Janet L Coppins
(74) *Attorney, Agent, or Firm*—Doina G. Ene; John E. Wurst; Kevin J. Forrestal

(57) ABSTRACT

Compounds of Formula 1

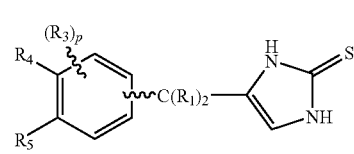

Formula 1 where the variables have the meaning defined in the specification are agonists of alpha$_2$ adrenergic receptors. Several compounds of the disclosure are specific or selective to alpha$_{2B}$ and/or alpha$_{2C}$ adrenergic receptors in preference over alpha$_{2A}$ adrenergic receptors. Additionally some of the claimed compounds have no or only minimal cardiovascular and/or sedatory activity. The compounds of Formula 1 are useful as medicaments in mammals, including humans, for treatment of diseases and or alleviations of conditions which are responsive to treatment by agonists of alpha$_2$ adrenergic receptors. Compounds of Formula 1 which have no significant cardiovascular and/or sedatory activity are useful for treating pain and other conditions with minimal side effects.

5 Claims, No Drawings

OTHER PUBLICATIONS

Minami et al, "Allodynia evoked by intrathecal administration of prostaglandin $E_2$ to conscious mice", 1994, 57 Pain, 217-223.

Kruse et al., STN International HCAPLUS Database, Columbus, OH, accession No. 1989: 439367.

Loksha et al., STN International HCAPLUS Database, Columbus, OH, accession No. 2002: 389433.

Trojanowski, John Q. "Alzheimer's Disease, Parkinson's Disease, and Related Brain Disorders: Brief Overview for Patients and Caregivers," internet article, Oct. 1999, http://pennhealth.com.

* cited by examiner

4-(CONDENSED CYCLICMETHYL)-IMIDAZOLE-2-THIONES ACTING AS ALPHA2 ADRENERGIC AGONISTS

This application in a continuation application of U.S. application Ser. No. 11/232,383 filed 20 Sep. 2005 which claims priority to Provisional Patent Application 60/612,939, filed 24 Sep. 2004, both of which are incorporated by reference herein.

BACKGROUND OF THE INVENTION

1. Field of the Invention

The present invention relates to 4-(condensed cyclicmethyl)-imidazole-2-thiones and to their use as agonists, preferably specific or selective agonists of alpha$_{2B}$ and/or alpha$_{2C}$ adrenergic receptors. More specifically the present invention relates to the above-noted compounds, to pharmaceutical compositions containing these compounds as active ingredient for modulating the alpha$_2$ adrenergic receptors, and even more specifically for utilizing these compounds and pharmaceutical compositions to alleviate chronic pain, allodynia, muscle spasticity, diarrhea, neuropathic pain and other diseases and conditions.

2. Background Art

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction).

For a further general background on the α-adrenergic receptors, the reader's attention is directed to Robert R. Ruffolo, Jr., α-Adrenoreceptors: Molecular Biology, Biochemistry and Pharmacology, (Progress in Basic and Clinical Pharmacology series, Karger, 1991), wherein the basis of $\alpha_1/\alpha_2$ subclassification, the molecular biology, signal transduction, agonist structure-activity relationships, receptor functions, and therapeutic applications for compounds exhibiting α-adrenergic receptor affinity is explored.

The cloning, sequencing and expression of alpha receptor subtypes from animal tissues has led to the subclassification of the $\alpha_1$ adrenoreceptors into $\alpha_{1A}$, $\alpha_{1B}$, and $\alpha_{1D}$. Similarly, the $\alpha_2$ adrenoreceptors have also been classified $\alpha_{2A}$, $\alpha_{2B}$, and $\alpha_{2C}$ receptors. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Among other indications, such as the treatment of glaucoma, hypertension, sexual dysfunction, and depression, certain compounds having alpha$_2$ adrenergic receptor agonist activity are known analgesics. However, many compounds having such activity do not provide the activity and specificity desirable when treating disorders modulated by alpha$_2$ adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

PCT Publication WO 03/099795 published on Dec. 4, 2003 describes 4-(substituted cycloalkylmethyl) imidazole-2-thiones, 4-(substituted cycloalkenylmethyl) imidazole-2-thiones and related compounds and their use as specific or selective agonists of alpha$_{2B}$ and/or alpha$_{2C}$ adrenergic receptors.

PCT Publication WO 02/36162 published on May 10, 2002 discloses some cyloalkenyl-methyl-imidazoles, condensed cyclic-methyl imadazoles and an imidazole thione of the following structure

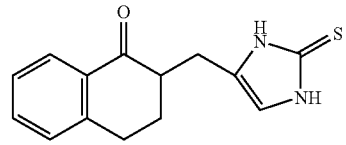

as an alpha$_{2B}$ or alpha$_{2C}$ selective agonist utilized for treatment of ocular neovascularization.

British Patent 1 499 485, published Feb. 1, 1978 describes certain thiocarbamide derivatives; some of these are said to be useful in the treatment of conditions such as hypertension, depression or pain.

PCT Publications WO01/00586 published on Jan. 4, 2001 and WO99/28300 published on Jun. 10, 1999 describe certain imidazole derivatives acting as agonists of alpha$_{2B}$ and/or alpha$_{2C}$ adrenergic receptors. U.S. Pat. No. 6,313,172 discloses phenylmethyl-thiourea derivatives used for treatment of pain.

U.S. Pat. No. 4,798,843 describes (phenyl)-imidazole-2-thiones and substituted (phenyl)-imidazole-2-thiones.

U.S. Pat. Nos. 6,545,182 and 6,313,172 describe phenylmethyl-(2-hydroxy)ethylthioureas which have no significant cardiovascular or sedative effects and are useful for alleviating chronic pain and allodynia. U.S. Pat. No. 6,534,542 describes cycloalkyl, cycloalkenyl, cycloalkylmethyl and cycloalkenylmethyl (2-hydroxy)ethylthioureas and their use as specific or selective agonists of alpha$_{2B}$ adrenergic receptors.

SUMMARY OF THE INVENTION

The present invention is directed to compounds of Formula 1

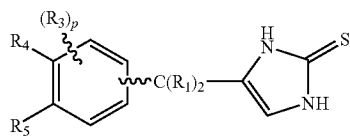

Formula 1 where $R_1$ is independently H, alkyl of 1 to 4 carbons, $CH_2OR_2$, or fluoro substituted alkyl of 1 to 4 carbons;

$R_2$ is independently H, alkyl of 1 to 4 carbons, $C(O)R_7$, carbocyclic aryl or heterocyclic aryl having 1 to 3 heteroatoms independently selected from N, O and S;

$R_3$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, $SR_2$;

p is an integer having the values of 0, 1, 2, or 3;

$R_4$ and $R_5$ together with the carbons to which they are attached jointly form a carbocyclic or a heterocyclic ring, the heterocyclic ring having 5 or 6 atoms in the ring and 1 to 3 heteroatoms independently selected from N, O and S;

said carbocyclic or heterocyclic ring jointly formed by $R_4$ and $R_5$ being optionally substituted with 1 to 7 $R_8$ groups;

$R_6$ is independently H, alkyl of 1 to 4 carbons, carbocyclic aryl or heterocyclic aryl having 1 to 3 heteroatoms independently selected from N, O and S;

$R_7$ is H or alkyl of 1 to 4 carbons, and $R_8$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, $SR_2$ or $R_8$ is O or S double-bonded to one carbon of said carbocyclic or heterocyclic ring.

In a second aspect the present invention is directed to pharmaceutical compositions containing as the active ingredient one or more compounds of Formula 1, the compositions being utilized as medicaments in mammals, including humans, for treatment of diseases and or alleviations of conditions which are responsive to treatment by agonists of alpha$_2$ adrenergic receptors. The compositions containing the compounds of the invention are primarily, but not exclusively, used for alleviation of chronic pain and/or allodynia. Some of the compounds of the invention have the demonstrable advantageous property that they are specific or selective to alpha$_{2B}$ and/or alpha$_{2C}$ adrenergic receptors in preference over alpha$_{2A}$ adrenergic receptors. In addition some of the alpha 2 agonist compounds have no or only minimal cardiovascular and/or sedatory activity.

DETAILED DESCRIPTION OF THE INVENTION

A general description of the compounds of the invention is provided in the Summary section of the present application for patent with reference to Formula 1. It will be readily apparent to those skilled in the art that some of the compounds depicted in these formulas may exist in trans (E) and cis (Z) isomeric forms. Moreover, some of the compounds of the invention may contain one or more asymmetric centers, such that the compounds may exist in enantiomeric as well as in diastereomeric forms. Unless it is specifically noted otherwise, the scope of the present invention includes all trans (E) and cis (Z) isomers, enantiomers, diastereomers and racemic mixtures. Some of the compounds of the invention may form salts with pharmaceutically acceptable acid or base, and such pharmaceutically acceptable salts of the compounds of Formula 1 are also within the scope of the invention.

The imidazole-2-thione compounds of the present invention can undergo tautomeric transformations and can be depicted by the tautomeric formulas shown below. All tautomers of Formula 1 are within the scope of the invention.

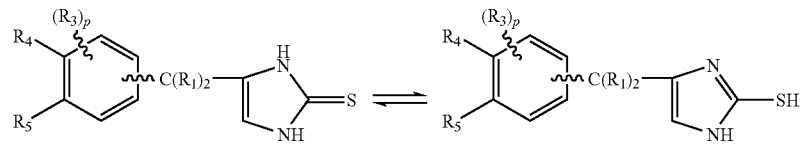

Formula 1          tautomeric Formula 1

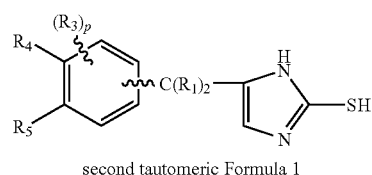

second tautomeric Formula 1

Generally speaking and referring to Formula 1, in the preferred compounds of the invention the variable $R_1$ is H, alkyl of 1 to 4 carbons, or $CH_2OR_2$. Even more preferably one of the $R_1$ groups is H and the other is alkyl of 1 to 4 carbons. Still more preferably one of the $R_1$ groups is methyl and the other is H. Compounds of the invention are equally preferred where both $R_1$ groups are hydrogen.

The variable p in the presently preferred compounds of the invention is zero (0), meaning that there usually is no $R_3$ substituent on the aromatic portion of the condensed cyclic moiety in the compounds of the invention. When there is an $R_3$ substituent then it is preferably alkyl of 1 to 4 carbons, or halogen and p is 1 or 2.

The variables $R_4$ and $R_5$ together with the carbons to which they are respectively attached form a or 6 membered ring and thereby, together with the 6-membered carbocyclic aromatic ring, form an annulated or condensed cyclic moiety. The 5 or 6 membered ring formed by $R_4$ and $R_5$ can be carbocyclic or heterocyclic, aromatic or non-aromatic, which are equally preferred. When the annulating ring formed by $R_4$ and $R_5$ is heterocyclic then 1 or 2 heteroatoms are preferred in that ring. Presently preferred heteroatoms are nitrogen, oxygen and sulfur.

The optional substituent Rx is not present in the presently preferred compounds. When the Rx group is present it is preferably, alkyl of 1 to 4 carbons, halogen, or O or S double bonded to a ring carbon.

Other compounds have the formula

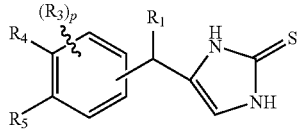

wherein $R_1$ is methyl or H, and p is 0 or 1.

Other compounds have the formula

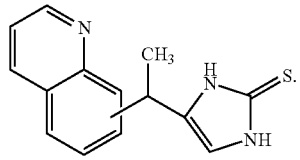

In other words, any of the compounds shown below are possible.

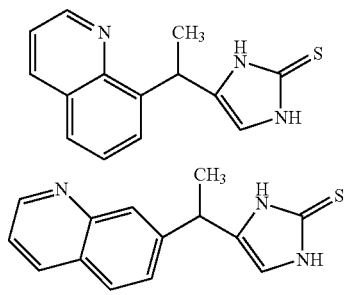

-continued

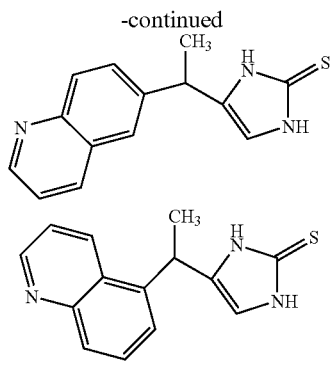

Specifically Contemplated Embodiments

In addition to those embodiments disclosed elsewhere herein. The following embodiments are specifically contemplated.

Compound Embodiments

One embodiment is a compound of the formula

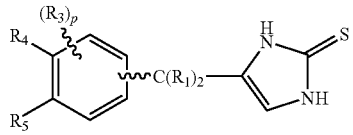

where $R_1$ is independently H, alkyl of 1 to 4 carbons, $CH_2OR_2$, or fluoro substituted alkyl of 1 to 4 carbons;

$R_2$ is independently H, alkyl of 1 to 4 carbons, $C(O)R_7$, carbocyclic aryl or heterocyclic aryl having 1 to 3 heteroatoms independently selected from N, O and S;

$R_3$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, $SR_2$;

p is an integer having the values of 0, 1, 2, or 3;

$R_4$ and $R_5$ together with the carbons to which they are attached jointly form a carbocyclic or a heterocyclic ring, the heterocyclic ring having 5 or 6 atoms in the ring and 1 to 3 heteroatoms independently selected from N, O and S;

said carbocyclic or heterocyclic ring jointly formed by R4 and R5 being optionally substituted with 1 to 7 $R_8$ groups;

$R_6$ is independently H, alkyl of 1 to 4 carbons, carbocyclic aryl or heterocyclic aryl having 1 to 3 heteroatoms independently selected from N, O and S;

$R_7$ is H or alkyl of 1 to 4 carbons, and $R_8$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, $SR_2$ or $R_8$ is O or S double bonded to one carbon of said carbocyclic or heterocyclic ring.

Another embodiment is a compound as described above having the formula

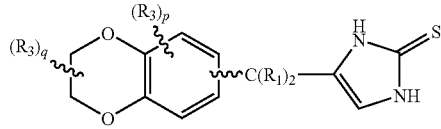

where q is an integer selected from 0, 1, 2, 3, and 4; and $R_1$, $R_3$, and p are as described above. Another embodiment is a compound as describe above having the formula

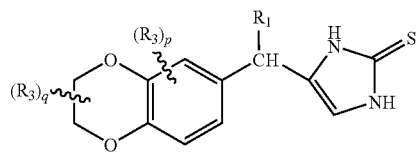

wherein $R_1$, $R_3$, and p are as described above, and q is an integer selected from 0, 1, 2, 3, and 4.

Another embodiment is a compound having the formula

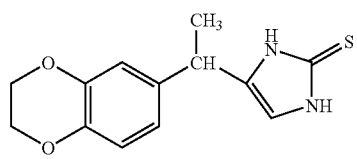

Another embodiment is a compound having the formula

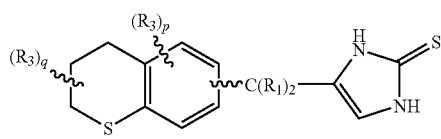

where q is an integer selected from 0, 1, 2, 3, 4, 5 and 6; and $R_1$, $R_3$ and p are as described above.

Another embodiment is a compound having the formula

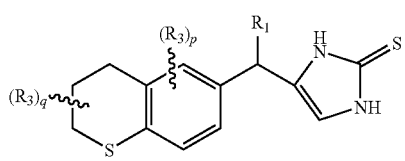

where q is an integer selected from 0, 1, 2, 3, 4, 5 and 6; and $R_1$, $R_3$ and p are as described above.

Another embodiment is a compound having the formula

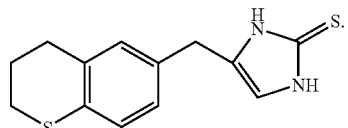

Another embodiment is a compound having the formula

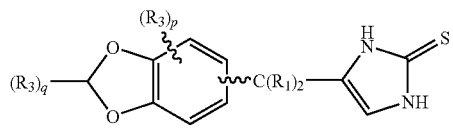

where q is an integer selected from 0, 1 and 2; and $R_1$, $R_3$, and p are as described above.

Another embodiment is a compound having the formula

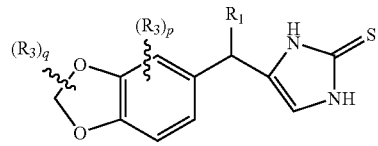

where q is an integer selected from 0, 1 and 2; and $R_1$, $R_3$, and p are as described above.

Another embodiment is a compound having the formula

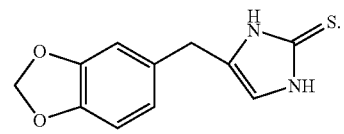

Another embodiment is a compound having the formula

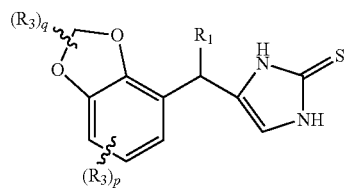

where q is an integer selected from 0, 1 and 2; and $R_1$, $R_3$, and p are as described above.

Another embodiment is a compound having the formula

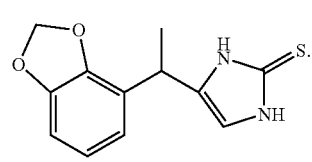

Another embodiment is a compound having the formula

[Structure: quinoline with $(R_3)_q$ and $(R_3)_p$ substituents, connected via $C(R_1)_2$ to imidazole-2-thione]

where q is an integer selected from 0, 1, 2 and 3; and $R_1$, $R_3$, and p are as described above.

Another embodiment is a compound having the formula

[Structure: quinoline with $(R_3)_q$ and $(R_3)_p$, connected via CH($R_1$) to imidazole-2-thione]

where q is an integer selected from 0, 1, 2 and 3; and $R_1$, $R_3$, and p are as described above.

Another embodiment is a compound having the formula

[Structure: 8-substituted quinoline-CH$_2$-imidazole-2-thione]

Another embodiment is a compound having the formula

[Structure: 8-substituted quinoline-CH(CH$_3$)-imidazole-2-thione]

Another embodiment is a compound having the formula

[Structure: quinoline with $(R_3)_q$ and $(R_3)_p$, connected via CH($R_1$) to imidazole-2-thione]

where q is an integer selected from 0, 1, 2 and 3; and $R_1$, $R_3$, and p are as described above.

Another embodiment is a compound having the formula

[Structure: 5-substituted quinoline-CH$_2$-imidazole-2-thione]

Another embodiment is a compound having the formula

[Structure: 5-substituted quinoline-CH(CH$_3$)-imidazole-2-thione]

In another embodiment, the compound above is a substantially pure dextrorotatory enantiomer.

In another embodiment, the compound above is a substantially pure levorotatory enantiomer.

Another embodiment is a compound having the formula

[Structure: benzodioxine with $(R_3)_q$ and $(R_3)_p$, connected via $C(R_1)_2$ to imidazole-2-thione]

where q is an integer selected from 0, 1, 2, 3 and 4; and $R_1$, $R_3$, and p are as described above.

Another embodiment is a compound having the formula

[Structure: benzodioxine with $(R_3)_q$ and $(R_3)_p$, connected via CH($R_1$) to imidazole-2-thione]

where q is an integer selected from 0, 1, 2, 3 and 4; and $R_1$, $R_3$, and p are as described above.

Another embodiment is a compound having the formula

[Structure: benzodioxine-CH$_2$-imidazole-2-thione]

Another embodiment is a compound having the formula

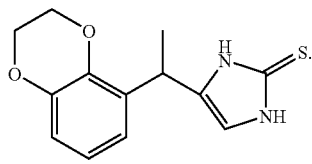

Another embodiment is a compound having the formula

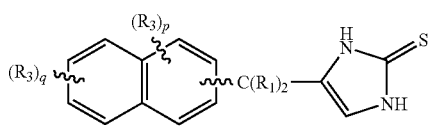

where q is an integer selected from 0, 1, 2, 3, and 4; and $R_1$, $R_3$, and p are as described above.

Another embodiment is a compound having the formula

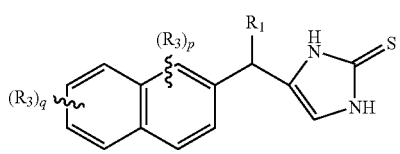

where q is an integer selected from 0, 1, 2, 3, and 4; and $R_1$, $R_3$, and p are as described above.

Another embodiment is a compound having the formula

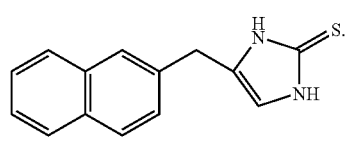

Another embodiment is a compound having the formula

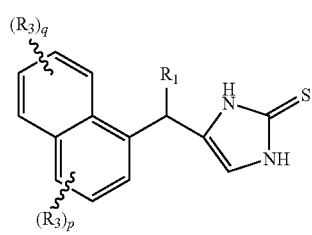

where q is an integer selected from 0, 1, 2, 3, and 4; and $R_1$, $R_3$, and p are as described above.

Another embodiment is a compound having the formula

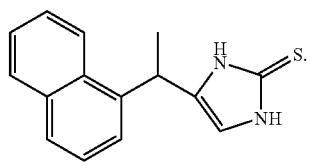

Another embodiment is a compound having the formula

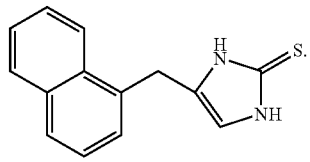

Another embodiment is a compound of the formula

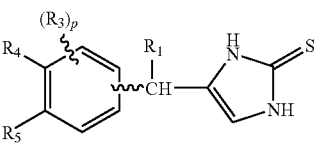

where $R_1$ is independently H, alkyl of 1 to 4 carbons, $CH_2OR_2$, or fluoro substituted alkyl of 1 to 4 carbons;

$R_2$ is independently H, alkyl of 1 to 4 carbons, $C(O)R_7$, carbocyclic aryl or heterocyclic aryl having 1 to 3 heteroatoms independently selected from N, O and S;

$R_3$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, $SR_2$;

p is an integer having the values of 0, 1, 2, or 3;

$R_4$ and $R_5$ together with the carbons to which they are attached jointly form a carbocyclic or a heterocyclic ring, the heterocyclic ring having 5 or 6 atoms in the ring and 1 to 3 heteroatoms independently selected from N, O and S;

said carbocyclic or heterocyclic ring jointly formed by R4 and R5 being optionally substituted with 1 to 7 $R_8$ groups;

$R_6$ is independently H, alkyl of 1 to 4 carbons, carbocyclic aryl or heterocyclic aryl having 1 to 3 heteroatoms independently selected from N, O and S;

$R_7$ is alkyl of 1 to 4 carbons, and $R_8$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, $SR_2$ or $R_8$ is O or S double bonded to one carbon of said carbocyclic or heterocyclic ring.

Another embodiment is a compound having the formula

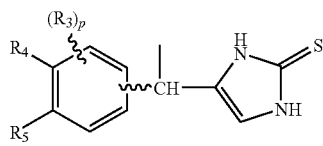

wherein $R_3$, $R_4$, $R_5$, and p are as described above.

Another embodiment is a compound having the formula

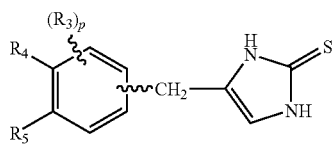

wherein $R_3$, $R_4$, $R_5$, and p are as described above.

Another embodiment is a compound having the formula

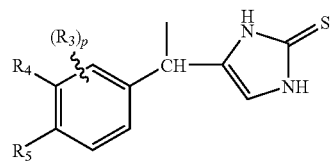

wherein $R_3$, $R_4$, $R_5$, and p are as described above.

Another embodiment is a compound having the formula

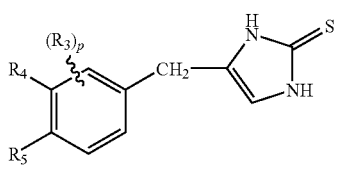

wherein $R_3$, $R_4$, $R_5$, and p are as described above.

Another embodiment is a compound having the formula

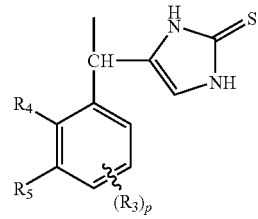

wherein $R_3$, $R_4$, $R_5$, and p are as described above.

Another embodiment is a compound having the formula

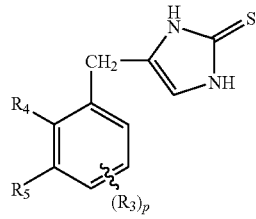

wherein $R_3$, $R_4$, $R_5$, and p are as described above.

Method Embodiments

One embodiment is a method of activating $alpha_{2B}$ or $alpha_{2C}$ adrenergic receptors in a mammal in need of such activation by administering to the mammal a pharmaceutical composition containing a therapeutically effective dose of a compound, said compound having the formula

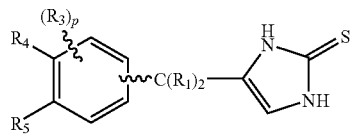

where $R_1$ is independently H, alkyl of 1 to 4 carbons, $CH_2OR_2$, or fluoro substituted alkyl of 1 to 4 carbons;

$R_2$ is independently H, alkyl of 1 to 4 carbons, $C(O)R_7$, carbocyclic aryl or heterocyclic aryl having 1 to 3 heteroatoms independently selected from N, O and S;

$R_3$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, $SR_2$;

p is an integer having the values of 0, 1, 2, or 3;

$R_4$ and $R_5$ together with the carbons to which they are attached jointly form a carbocyclic or a heterocyclic ring, the heterocyclic ring having 5 or 6 atoms in the ring and 1 to 3 heteroatoms independently selected from N, O and S;

said carbocyclic or heterocyclic ring jointly formed by R4 and R5 being optionally substituted with 1 to 7 $R_8$ groups;

$R_6$ is independently H, alkyl of 1 to 4 carbons, carbocyclic aryl or heterocyclic aryl having 1 to 3 heteroatoms independently selected from N, O and S;

$R_7$ is H or alkyl of 1 to 4 carbons, and $R_8$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, $SR_2$ or $R_8$ is O or S double bonded to one carbon of said carbocyclic or heterocyclic ring.

In another method the pharmaceutical composition is administered to the mammal to alleviate pain.

In another method the pharmaceutical composition is administered to the mammal to alleviate chronic pain.

In another method the pharmaceutical composition is administered to the mammal to alleviate allodynia.

In another method the pharmaceutical composition is administered orally.

In another method the pharmaceutical composition is administered intraperitonially.

In another method the mammal is administered the composition for treating a condition selected from the group consisting of chronic pain, visceral pain, neuropathic pain, corneal pain, glaucoma, elevated intraocular pressure, ischemic neuropathies, neurodegenerative diseases, diarrhea, nasal congestion, muscle spasticity, diuresis, withdrawal syndromes, neurodegenerative diseases, optic neuropathy, spinal ischemia, stroke, memory and cognition deficits, attention deficit disorder, psychoses, manic disorders, anxiety, depression, hypertension, congestive heart failure, cardiac ischemia, arthritis, spondylitis, gouty arthritis, osteoarthritis, juvenile arthritis, autoimmune diseases, lupus erythematosus, chronic gastrointestinal inflammations, Crohn's disease, gastritis, irritable bowel syndrome (IBS), functional dyspepsia and ulcerative colitis.

In another method the mammal is administered the composition for treating glaucoma.

In another method the mammal is administered the composition for treating neuropathies or neurodegenerative diseases.

In another method the mammal is administered the composition for treating muscle spasticity.

The presently most preferred compounds of the invention are disclosed by their structural formulas in Table 1 together with their activity in assays measuring their ability to act as agonists of alpha$_{2A}$, alpha$_{2B}$ and alpha$_{2C}$ adrenergic receptors.

TABLE 1

| Biological Data: Intrinsic Activity | | | |
|---|---|---|---|
| Structure | Alpha 2A | Alpha 2B | Alpha 2C |
| 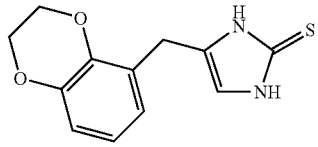<br>Compound 1 | 0.44 | 0.94 | 0.56 |
| 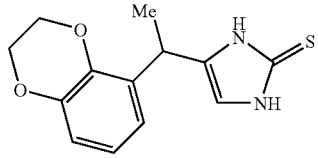<br>Compound 2 | 0.45 | 1.38 | 0.48 |
| 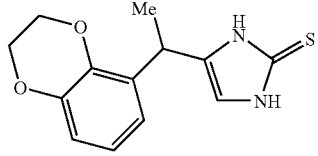<br>Compound 3 | 0.56 | 0.97 | 0.77 |

TABLE 1-continued

| Biological Data: Intrinsic Activity | | | |
|---|---|---|---|
| Structure | Alpha 2A | Alpha 2B | Alpha 2C |
| 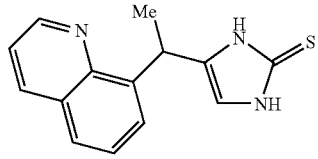<br>Compound 4 | 0.80 | 1.03 | 0.62 |
| 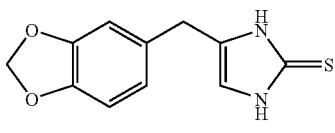<br>Compound 5 | NA | 1.05 | NA |
| 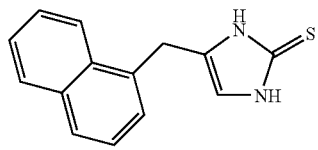<br>Compound 6 | 0.48 | 0.73 | 0.55 |
| 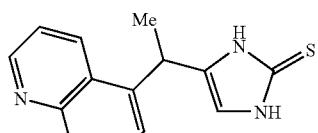<br>Compound 7 | NA | 0.90 | NA |
| 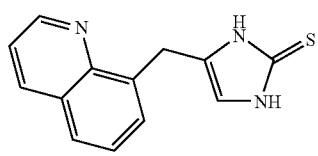<br>Compound 8 | 0.93 | 1.01 | 0.75 |
| 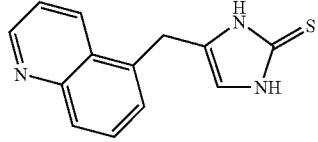<br>Compound 9 | NA | 0.74 | NA |
| 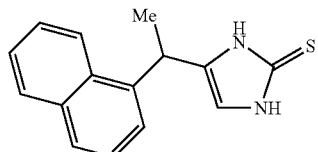<br>Compound 10 | 0.52 | 1.21 | NA |

TABLE 1-continued

Biological Data: Intrinsic Activity

| Structure | Alpha 2A | Alpha 2B | Alpha 2C |
|---|---|---|---|
| Compound 11 | NA | 0.94 | NA |
| Compound 12 | 0.54 | 1.15 | NA |
| Compound 13 | NA | 0.95 | NA |
| Compound 14 (+) | NA | 0.86 | NA |
| Compound 15 (−) | NA | 0.89 | NA |
| Compound-16 | NA | 1.22 | 0.69 |
| Compound-17 | NA | 0.98 | NA |
| Compound-18 | 0.80 | 1.05 | 0.41 |

General Methods for Obtaining the Compounds of the Invention

Reaction Schemes A-E illustrate general methods for obtaining the 4-(carbo-bicyclyl)-imidazole-2-thiones and 4-(hetero-bicyclyl)-imidazole-2-thiones.

Reaction Scheme A provides a general method for preparing compounds of Formula 1 where either both $R_1$ group represent hydrogen, or one $R_1$ group represent hydrogen and the other an alkyl group or other group defined in Formula 1 for the variable $R_1$. The remaining variables in Reaction Scheme A are defined in the same manner as in connection with Formula 1. An aldehyde or ketone of Formula 2 is the starting material which can be obtained through commercial sources or prepared in accordance with known procedures in the chemical scientific and patent literature or by modifications of known procedures which are readily apparent to the practicing synthetic organic chemist. The aldehyde or ketone of Formula 2 is reacted with a Grignard reagent of 4-iodo-1-triphenylmethyl-1H-imidazole to provide the triphenylmethyl (trityl) protected hydroxyimidazole compounds of Formula 3. Deoxygenation of the bridging hydroxyl moiety was accomplished by methods such as treatment with trifluoroacetic acid (TFA) in triethyl silane ($Et_3SiH$) or oxidation of the alcohol to a ketone which can be reduced with a Huang-Minlon modification of the Wolff-Kishner reduction, followed by acidic deprotection of the trityl group to produce imidazoles of Formula 4. The imidazoles of Formula 4 are reacted with phenyl chlorothionoformate in the presence of sodium bicarbonate and water and subsequently treated with a base, such as triethylamine to produce 4-(carbo-bicyclyl)-imidazole-2-thiones and 4-(hetero-bicyclyl)-imidazole-2-thiones of Formula 5. The compounds of Formula 5 are within the scope of the present invention.

Reaction Scheme A

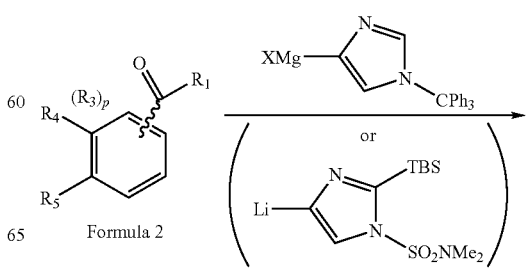

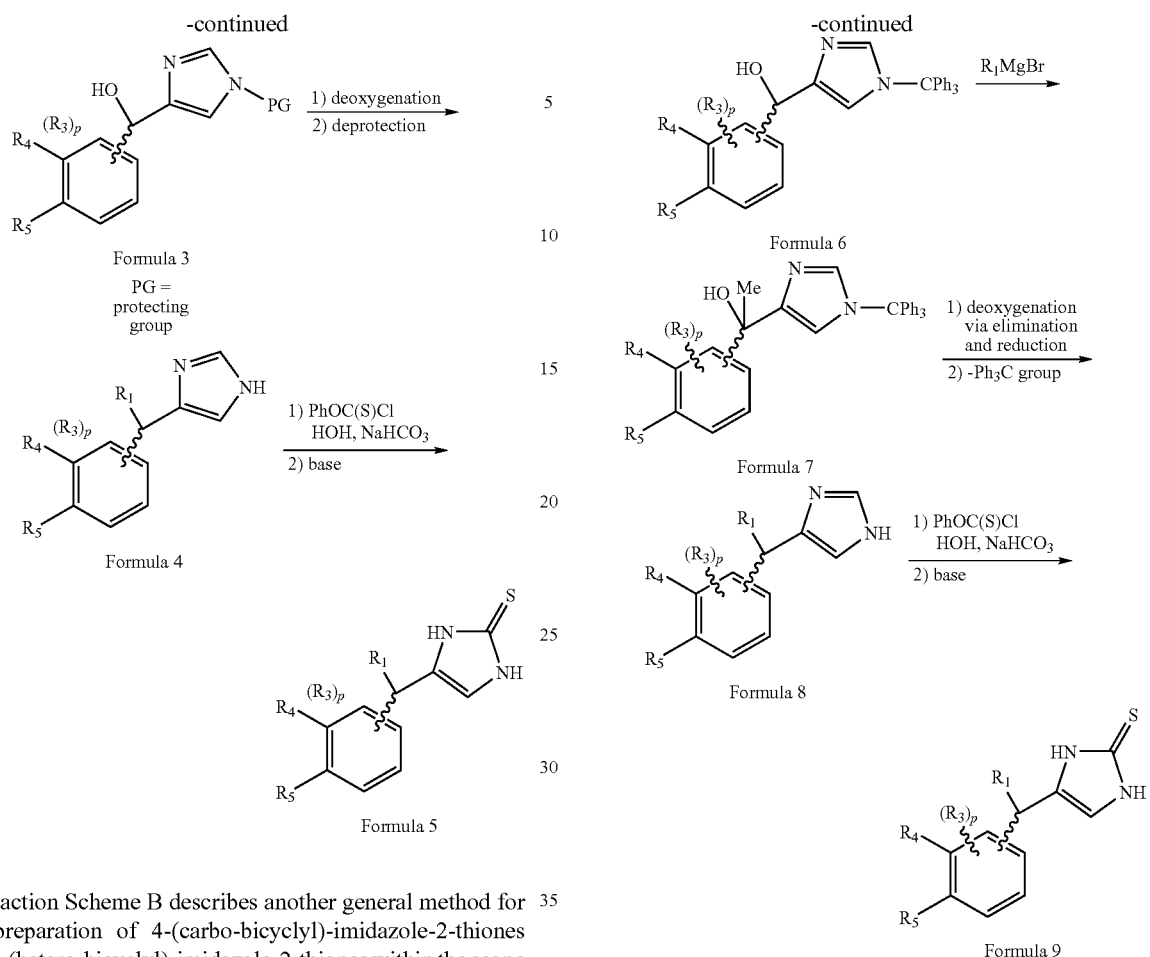

Reaction Scheme B describes another general method for the preparation of 4-(carbo-bicyclyl)-imidazole-2-thiones and 4-(hetero-bicyclyl)-imidazole-2-thiones within the scope of the present invention where one of the $R_1$ groups is hydrogen and the other is as defined in connection with Formula 1. In accordance with this scheme compounds of Formula 3, as prepared in Reaction Scheme A, are oxidized to the ketone compounds of Formula 6. Addition of a Grignard reagent ($R_1$MgBR) produces tertiary alcohols of Formula 7. Deoxygenation of the tertiary alcohols is conducted via an elimination/reduction methodology, and removal of the trityl protecting group is accomplished under acidic conditions to deliver imidazole compounds of Formula 8. The imidazoles of Formula 8 are reacted with phenyl chlorothionoformate in the presence of sodium bicarbonate and water and subsequently treated with a base, such as triethylamine to produce 4-(carbo-bicyclyl)-imidazole-2-thiones and 4-(hetero-bicyclyl)-imidazole-2-thiones of Formula 9.

Reaction Scheme C discloses still another general method for preparing compounds of the invention where one of the $R_1$ groups of Formula 1 is hydrogen and the other is as defined in connection with Formula 1. This scheme also employs an aldehyde starting material, of Formula 10, which can be obtained through commercial sources or prepared in accordance with known procedures in the chemical scientific and patent literature or by modifications of known procedures which are readily apparent to the practicing synthetic organic chemist. The aldehyde of Formula 10 is reacted with tosyl methylisocyanide, (TosMIC) and sodium cyanide and thereafter heated in the presence of excess ammonia to produce the imidazole compounds of Formula 11. The imidazoles of Formula 11 are reacted with phenychlorothionoformate as described above to obtain compounds of Formula 12.

Reaction Scheme B

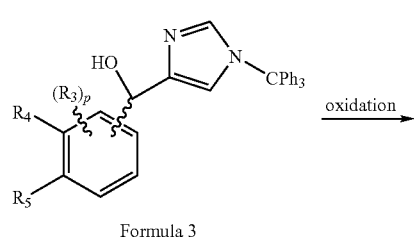

Formula 3

Reaction Scheme C

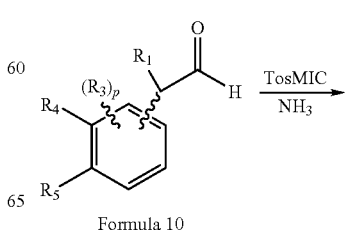

Formula 10

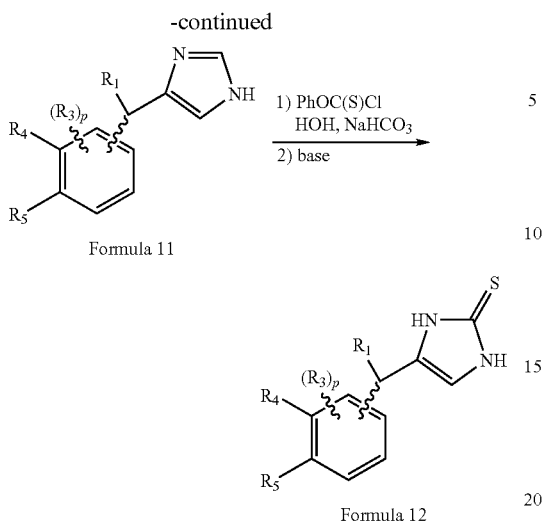

Formula 11

Formula 12

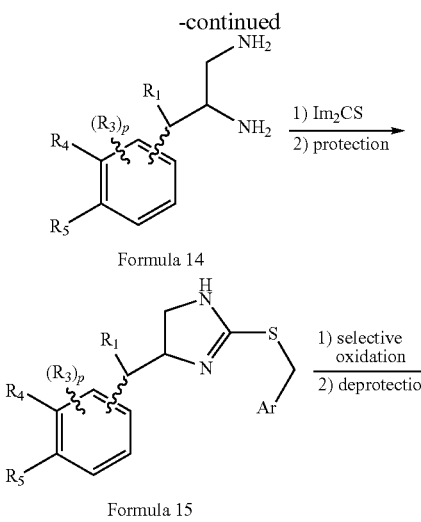

Formula 14

Formula 15

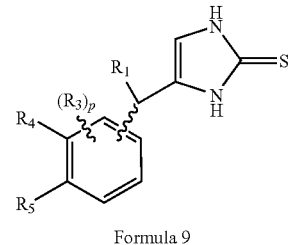

Formula 9

Reaction Scheme D is yet another general method for preparing compounds of the invention where one of the $R_1$ groups of Formula 1 is hydrogen and the other is as defined in connection with Formula 1. This scheme also employs the aldehyde of Formula 2 as starting material. The aldehyde of Formula 2 is reacted with a Grignard reagent ($R_1MgBr$) and the resulting alcohol is converted to the corresponding chloro compound by the action of thionyl chloride. Nucleophilic displacement of the chloride with the lithium anion of N-(diphenylmethylene)aminoacetonitrile and hydrolysis produces the amino nitrile compound of Formula 13. A selective reduction (eg. Raney Ni 2800 with amine additives) produces the diamine compounds of Formula 14. Reaction of the diamines of Formula 15 with thiocarbonyl-diimidazole and protection of the thione with p-methoxybenzylchloride yields compounds of Formula 15. The compounds of Formula 15 are oxidized with a Swern-type reagent and deprotected under acidic conditions to give compounds of Formula 9.

Reaction Scheme E discloses a general method for preparing compounds of the invention where both of the $R_1$ groups of Formula 1 are hydrogen. Reaction Scheme E is the inverse of Scheme A where the nucleophile (Formula 16) is generated on the general aromatic component. This nucleophile (Formula 16) is added to the carbonyl that is appended onto the protected imidazole compound (Formula 17). Conversion of intermediates such as Formula 17 is completed by methods found in Reaction Scheme A to form compounds of Formula 18.

Reaction Scheme D

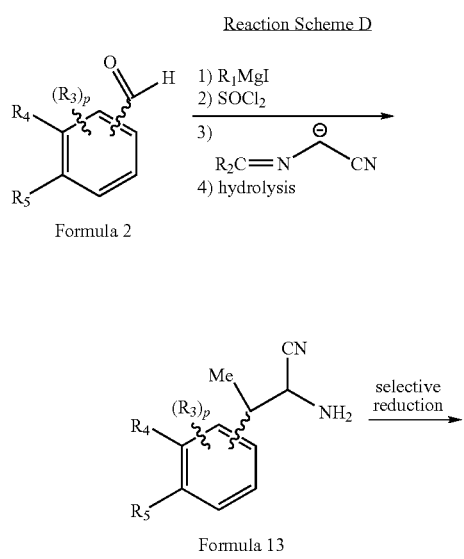

Formula 2

Formula 13

Reaction Scheme E

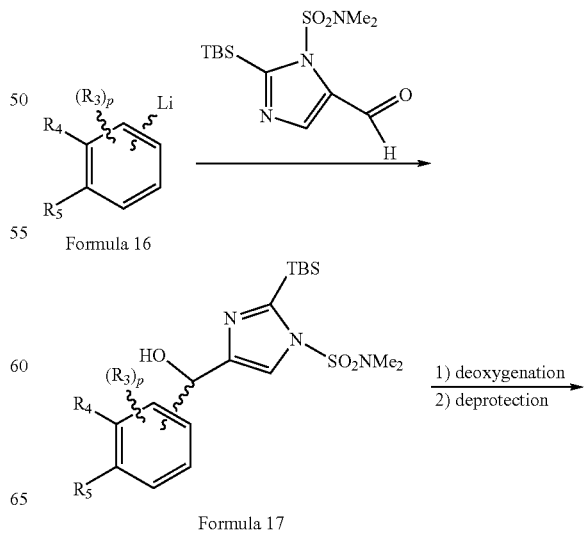

Formula 16

Formula 17

-continued
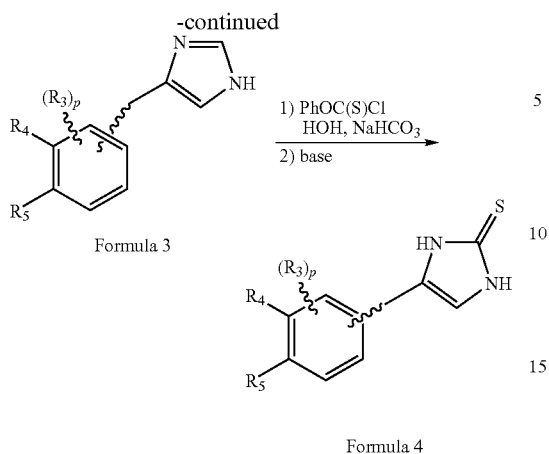
Example L
Method L: Procedure for the preparation of 4-Benzo[1,2,5]thiadiazol-4-ylmethyl-1,3-dihydro-imidazole-2-thione (Compound 16) and 4-(1-Benzo[1,2,5]thiadiazol-4-yl-ethyl)-1,3-dihydro-imidazole-2-thione (Compound 17)
Example L
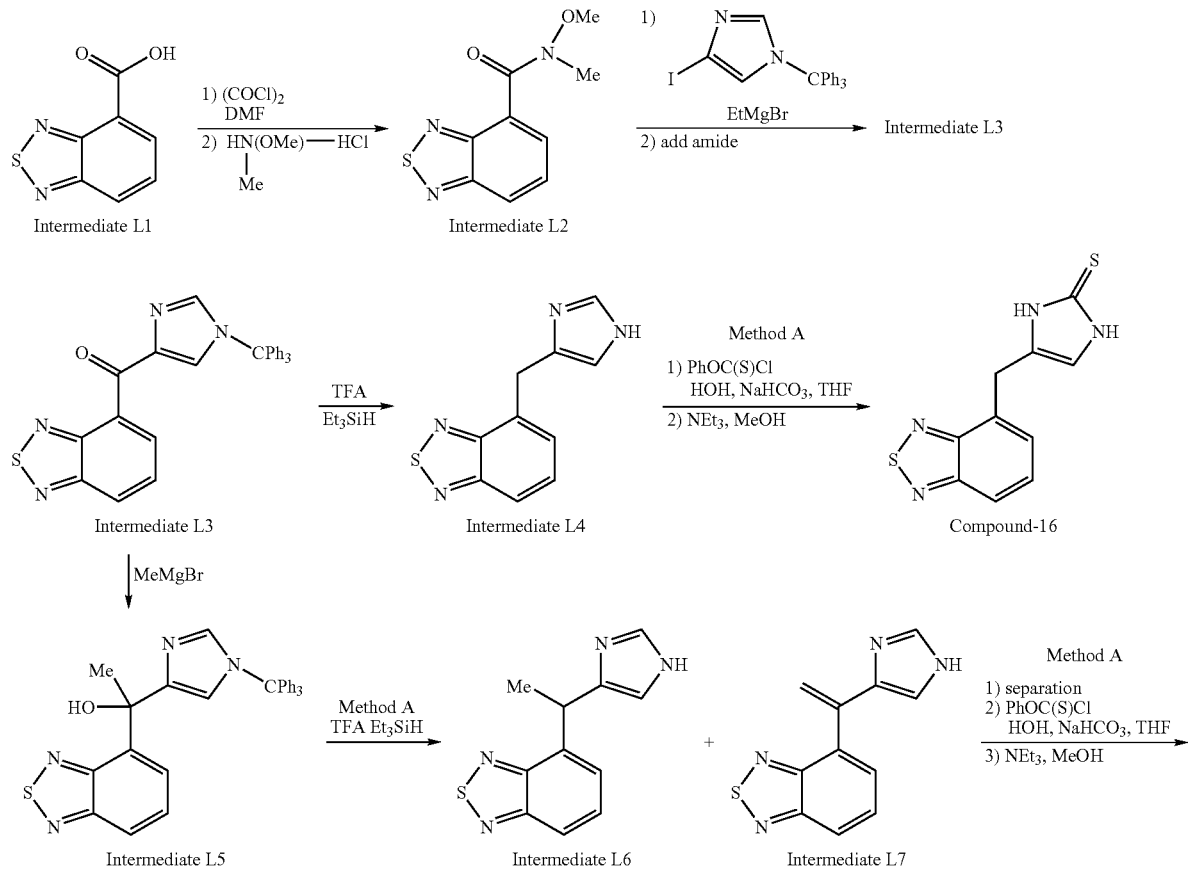

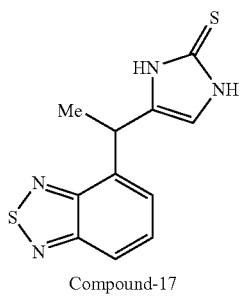

Compound-17

General Method for the Formation of Intermediate L3:

A suspension of benzo[1,2,5]thiadiazole-4-carboxylic acid (Intermediate L1) (1.8 g, 9.99 mmol) (commercially available from Maybridge) in benzene (100 mL) was treated with oxalyl chloride (5.1 mL of a 2 M CH$_2$Cl$_2$ solution) and DMF (catalytic amount) at rt for 1 h. The solvent was removed under vacuum and re-suspended in benzene. The mixture was decanted into a flask and concentrated under vacuum. The acid chloride intermediate was dissolved in chloroform (10 mL) and added to a solution of N,O-dimethylhydroxylamine-HCl (1.47 g, 15 mmol) (commercially available from Aldrich) and triethylamine (4 mL, 30 mmol) in chloroform (90 mL) at 0° C. The mixture was stirred at rt for 2 h. The mixture was subjected to a standard aqueous work-up. All solvent was removed under vacuum and the residue was purified by chromatography on silica gel with 50% EtOAc:hexane to give benzo[1,2,5]thiadiazole-4-carboxylic acid methoxy-methyl-amide (Intermediate L2) 2 g (90% over two steps).

A mixture of 4-iodo-1-tritylimidazole (commercially available from Synchem) (6.3 g, 14.4 mmol) in dichloromethane (100 mL) at rt was treated with ethyl magnesium bromide (4.8 mL, 14.4 mmol, 3M in THF) and allowed to react for 1 h. A solution of benzo[1,2,5]thiadiazole-4-carboxylic acid methoxy-methyl-amide (Intermediate L2) (2.0 g, 9.0 mmol) in dichloromethane (50 mL) was added via syringe at rt and stirred for 40 m. The residue was isolated in a typical aqueous workup and purified by chromatography on silica gel with 30% EtOAc:hexane to give benzo[1,2,5]thiadiazol-4-yl-(1-trityl-1H-imidazol-4-yl)-methanone (Intermediate L3), 1 g (25%).

Conversion of Intermediate L3 to 4-Benzo[1,2,5]thiadiazol-4-ylmethyl-1,3-dihydro-imidazole-2-thione (Compound 16)

A solution of benzo[1,2,5]thiadiazol-4-yl-(1-trityl-1H-imidazol-4-yl)-methanone (Intermediate L3) (500 mg, 1.12 mmol) in methylene chloride (2 mL) was treated with triethylsilane (8 mL), and trifluoroacetic acid (8 mL) at rt for 48 h. This mixture was evaporated under vacuum and quenched with a ~7M NH$_3$-MeOH solution. The solvent was exchanged with CH$_2$Cl$_2$. The solution was concentrated onto silica gel and purified by chromatography, eluting with 3% NH$_3$-MeOH:CH$_2$Cl$_2$ to give 4-(1H-imidazol-4-ylmethyl)-benzo[1,2,5]thiadiazole (Intermediate L4). 4-(1H-imidazol-4-ylmethyl)-benzo[1,2,5]thiadiazole (Intermediate L4) was subjected to the appropriate process steps in Method A to produce 4-benzo[1,2,5]thiadiazol-4-ylmethyl-1,3-dihydro-imidazole-2-thione (Compound 16).

$^1$H NMR (300 MHz, DMSO-d$^6$ w/TMS): δ 12.01 (s, 1H), 11.76 (s, 1H), 7.98 (d, J=9.0 Hz, 1H), 7.69 (t, J=8.7 Hz, 1H), 7.45 (d, J=6.6 Hz, 1H), 6.57 (s, 1H), 4.23 (s, 2H).

Conversion of Intermediate L3 to 4-Benzo[1,2,5]thiadiazol-4-ylmethyl-1,3-dihydro-imidazole-2-thione (Compound 17)

A solution of benzo[1,2,5]thiadiazol-4-yl-(1-trityl-1H-imidazol-4-yl)-methanone (Intermediate L3) (448 mg, 1.0 mmol) in THF (20 mL) at −15° C. was treated with MeMgBr (0.7 mL, 3M in ether) for ~1 h. The reaction mixture was quenched with water and some sodium bicarbonate. The layers were separated and dried over MgSO$_4$, filtered, evaporated and purified by column chromatography on silica gel with 60% EtOAc: hexanes. This gave 1-benzo[1,2,5]thiadiazol-4-yl-1-(1-trityl-1H-imidazol-4-yl)-ethanol (Intermediate L5) 130 mg (25%).

1-Benzo[1,2,5]thiadiazol-4-yl-1-(1-trityl-1H-imidazol-4-yl)-ethanol (Intermediate L5) was subjected to the appropriate process steps in Method A to produce 4-(1-benzo[1,2,5]thiadiazol-4-yl-ethyl)-1,3-dihydro-imidazole-2-thione (Compound 17).

$^1$H NMR (300 MHz, CDCl$_3$ w/TMS): δ 10.76 (brs, 1H), 10.50 (brs, 1H), 7.90 (d, J=8.7 Hz, 1H), 7.53 (t, J=5.1 Hz, 1H), 7.38 (d, J=7.2 Hz, 1H), 6.55 (s, 1H), 4.75 (q, J=6.9 Hz, 1H), 1.75 (d, J=7.5 Hz, 2H).

Method M: Procedure for the Preparation of 4-[1-(8-methyl-quinolin-7-yl)-ethyl]-1,3-dihydro-imidazole-2-thione (Compound 18)

Example M

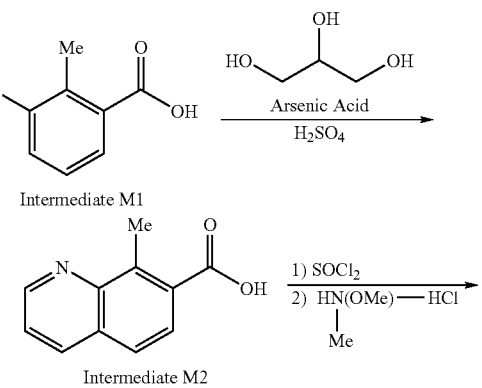

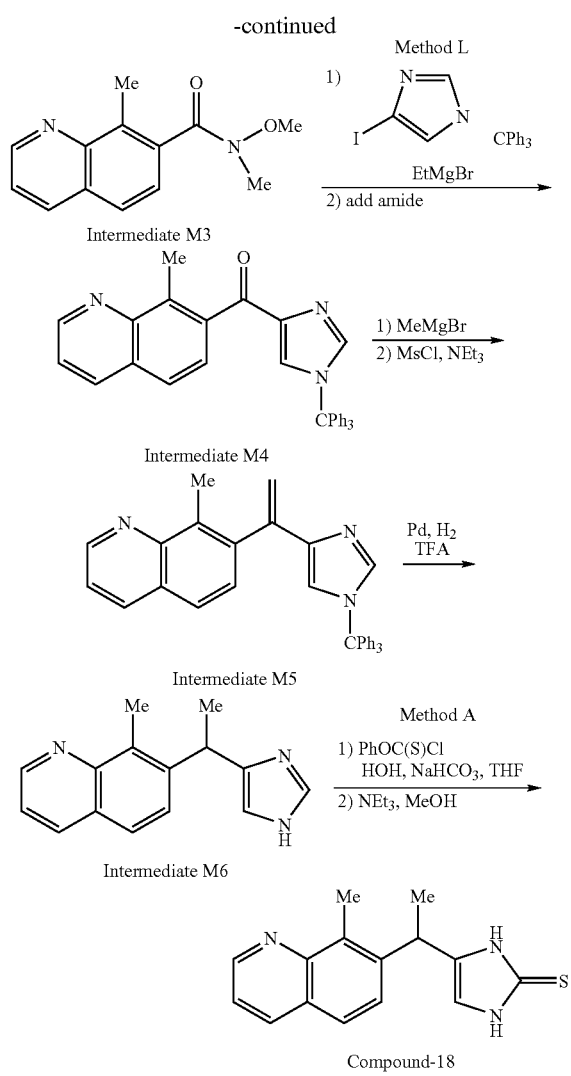

A mixture of 3-amino-2-methylbenzoic acid (Intermediate M1) (6.06 g, 39.6 mmol) (commercially available from Aldrich) and arsenic acid ($H_5AS_3O_{10}$) 7.43 g (commercially available from VWR/ALFA) in glycerol (5.8 mL, 79.2 mmol), and sulfuric acid (9 mL) was heated to 160° C. for 5 h. The mixture was cooled to rt, diluted with water and filtered through a bed of diatomaceous earth. The pH was adjusted to pH 6-7 with 2 M NaOH. The aqueous layer was exhaustively extracted with $CHCl_3$:MeOH (3:1). The organic fractions were pooled and evaporated under vacuum to give a solid. This solid was titurated with $CHCl_3$, and collected on a glass frit. The solid material was washed with hexanes and dried under high vacuum to give a pure solid, 8-methylquinoline-7-carboxylic acid (intermediate M2) 3.86 g (51%).

A solution of 8-methylquinoline-7-carboxylic acid (Intermediate M2) (3.86 g, 20.6 mmol) in thionyl chloride (15 mL) was heated to reflux for 1 h. The mixture was cooled to rt and concentrated under vacuum. The material was diluted in $CH_2Cl_2$ and decanted into a clean flask. The mixture was treated with N,O-dimethylhydroxylamine-HCl (3.0 g, 30.1 mmol) and triethylamine (10.6 mL, 76 mmol) at 0° C. The mixture was stirred at rt for several h. After a typical aqueous work-up, the residue was purified by chromatography on silica gel with 50 to 60% EtOAc:hexane to give N-methoxy-N-8-dimethylquinoline-7-carboxamide (Intermediate M3) 3.91 g (82% over two steps) as in Method L.

N-methoxy-N-8-dimethylquinoline-7-carboxamide (Intermediate M3) (3.91 g, 17 mmol) was subjected to the appropriate process steps in Method L to produce (8-methylquinolin-7-yl)(1-trityl-1H-imidazol-4-yl)methanone (Intermediate M4) 3.59 g (44%).

A solution of (8-methylquinolin-7-yl)(1-trityl-1H-imidazol-4-yl)methanone (Intermediate M4) (3.59 g, 7.49 mmol) in THF (100 mL) at 0° C. was treated with MeMgBr (5.0 mL, 3M in ether) for 16 h. The reaction mixture was quenched with $NH_4Cl$ (aq) and extracted with EtOAc. The layers were separated and dried over $MgSO_4$, filtered, evaporated and purified by column chromatography on silica gel with 3 to 4% $NH_3$-MeOH. The alcohol in $CH_2Cl_2$ (100 mL) was treated with $Et_3N$ (8.4 mL, 60.3 mmol) and methane sulfonyl chloride (1.75 mL, 22.6 mmol) at 0° C. for 3 h. The mixture was quenched with water and extracted with $CH_2Cl_2$. The organic layers were pooled and evaporated to give 8-methyl-7-[1-(1-trityl-1H-imidazol-4-yl)vinyl]quinoline (Intermediate M5) 2.14 g (60% over two steps). This material was used in the next step without further purification.

A solution of 8-methyl-7-[1-(1-trityl-1H-imidazol-4-yl)vinyl]quinoline (Intermediate M5) (2.14 g, 4.49 mmol) in TFA (40 mL) was reduced by action of 10% Pd/C (0.51 g) under $H_2$ (45-50 psi) for 16 h at rt. The mixture was filtered through celite and the solvent was removed under vacuum. The residue was purified by chromatography on silica gel with 24% $NH_3$-MeOH:$CH_2Cl_2$ to give 7-[1-(1H-imidazol-4-yl)ethyl]-8-methylquinoline (Intermediate M6) 834 mg, (79%).

7-[1-(1H-Imidazol-4-yl)ethyl]-8-methylquinoline (Intermediate M6) was subjected to the appropriate process steps in Method A to produce 4-[1-(8-methyl-quinolin-7-yl)-ethyl]-1,3-dihydro-imidazole-2-thione (Compound 18).

$^1$H NMR (300 MHz, $CD_3OD$): δ 11.91 (brs, 1H), 11.77 (brs, 1H), 8.92 (dd, J=4.2, 1.8 Hz, 1H), 8.28 (dd, J=8.4, 1.8 Hz, 1H), 7.76 (d, J=8.7 Hz, 1H), 7.49 (dd, J=8.1, 4.2 Hz, 1H), 7.36 (d, J=8.4 Hz, 1H), 6.69 (s, 1H), 4.44 (q, J=7.2 Hz, 1H), 2.82 (s, 3H), 1.49 (d, J=7.2 Hz, 3H).

Biological Activity, Modes of Administration

The imidazole-2-thione compounds of the invention are agonists of alpha$_2$ adrenergic receptors. Many compounds of the invention are specific or selective agonists of alpha$_{2B}$ and/or to a lesser extent alpha$_{2C}$ adrenergic receptors, in preference over alpha$_{2A}$ adrenergic receptors. The specific or selective alpha$_{2B}$ and/or to a lesser extent alpha$_{2C}$ agonist activity of the compounds of the invention is demonstrated in an assay titled Receptor Selection and Amplification technology (RSAT) assay, which is described in the publication by Messier et. al., 1995, Pharmacol. Toxicol. 76, pp. 308-311 (incorporated herein by reference) and is also described below. Another reference pertinent to this assay is Conklin et al. (1993) Nature 363:274-6, Receptor Selection and Amplification Technology (RSAT) assay, also incorporated herein by reference.

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, Gq, elicit this response. Alpha$_2$ receptors, which normally couple to Gi, activate the RSAT response when coexpressed with a hybrid Gq protein that has a Gi receptor recognition domain, called Gq/i5.

NIH-3T3 cells are plated at a density of $2 \times 10^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μl aliquots of various concentrations of drugs in triplicate in 96-well dishes. Incubations continue 72-96 hr at 37° C. After washing with phosphate-buffered saline, β-galactosidase enzyme activity is determined by adding 200 μl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the $alpha_{2A}$, $alpha_{2B}$ and $alpha_{2C}$ receptors.

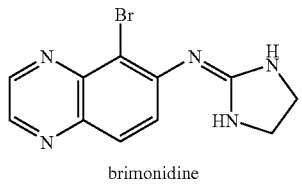

brimonidine

Diseases that may be treated with this invention include, but are not limited to neurodegenerative aspects of the following conditions:

MACULOPATHIES/RETINAL DEGENERATION Non-Exudative Age Related Macular Degeneration (ARMD), Exudative Age Related Macular Degeneration (ARMD), Choroidal Neovascularization, Diabetic Retinopathy, Central Serous Chorioretinopathy, Cystoid Macular Edema, Diabetic Macular Edema, Myopic Retinal Degeneration, UVEITIS/RETINITIS/CHOROIDITIS/OTHER INFLAMMATORY DISEASES Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome, Punctate Inner Choroidopathy, Acute Posterior Multifocal Placoid Pigment Epitheliopathy, Acute Retinal Pigement Epitheliitis, Acute Macular Neuroretinopathy VASCULAR DISEASES/EXUDATIVE DISEASES Diabetic retinopathy, Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy, Eales Disease TRAUMATIC/SURGICAL/ENVIRONMENTAL Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy PROLIFERATIVE DISORDERS Proliferative Vitreal Retinopathy and Epiretinal Membranes INFECTIOUS DISORDERS Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associate with HIV Infection, Uveitic Disease Associate with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis GENETIC DISORDERS Retinitis Pigmentosa, Systemic Disorders with Associated Retinal Dystrophies, Congenital Stationary Night Blindness, Cone Dystrophies, Stargardt's Disease And Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum RETINAL TEARS/HOLES Retinal Detachment, Macular Hole, Giant Retinal Tear TUMORS Retinal Disease Associated With Tumors, Congenital Hypertrophy Of The RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

The results of the RSAT assay with several exemplary compounds of the invention are disclosed in Table 1 above together with the chemical formulas of these exemplary compounds. NA stands for "not active" at concentrations less than 10 micromolar.

Generally speaking $alpha_2$ agonists, can alleviate sympathetically-sensitized conditions that are typically associated with periods of stress. These include neurological conditions of: 1) increased sensitivity to stimuli such as intracranial pressure, light and noise characteristic of migraines and other headaches; 2) the increased sensitivity to colonic stimuli characteristic of Irritable Bowel Syndrome and other GI disorders such as functional dyspepsia; 3) the sensation of itch associated with psoriasis and other dermatological conditions; 4) muscle tightness and spasticity; 5) sensitivity to normally innocuous stimuli such as light touch and spontaneous pain characteristic of conditions like fibromyalgia; 6) various cardiovascular disorders involving hypertension, tachycardia, cardiac ischemia and peripheral vasoconstriction; 7) metabolic disorders including obesity and insulin resistance; 8) behavioral disorders such as drug and alcohol dependence, obsessive-compulsive disorder, Tourette's syndrome, attention deficit disorder, anxiety and depression; 9) altered function of the immune system such as autoimmune diseases including lupus erythematosis and dry eye disorders; 10) chronic inflammatory disorders such as Crohn's disease and gastritis; 11) sweating (hyperhydrosis) and shivering; and 12) sexual dysfunction.

Alpha$_2$ agonists including alpha$_{2B/2C}$ agonists are also useful in the treatment of glaucoma, elevated intraocular pressure, neurodegenerative diseases including Alzheimer's, Parkinsons, ALS, schizophrenia, ischemic nerve injury such as stroke or spinal injury, and retinal injury as occurs in glaucoma, macular degeneration, diabetic retinopathy, retinal dystrophies, Lebers optic neuropathy, other optic neuropathies, optic neuritis often associated with multiple sclerosis, retinal vein occlusions, and following procedures such as photodynamic therapy and LASIX. Also included are chronic pain conditions such as cancer pain, post-operative pain, allodynic pain, neuropathic pain, CRPS or causalgia, visceral pain.

A compound is considered selective agonist of alpha$_{2B}$ and/or alpha$_{2C}$ adrenergic receptors in preference over alpha$_{2A}$ receptors, if the compound is more active, preferably at least ten (10) times more active towards either alpha$_{2B}$ or towards alpha$_{2C}$ receptors than towards alpha$_{2A}$ receptors. It can be seen from these tables that many compounds of the invention are specific or selective agonists of alpha$_{2B}$ and/or alpha$_{2C}$ adrenergic receptors within the former definition, and in fact have no agonist like activity or only insignificant agonist-like activity on alpha$_{2A}$ receptors.

Thus, the imidazole-2-thione compounds of the invention are useful for treating neurological conditions of conditions and diseases which are responsive to treatment by alpha$_2$ and particularly by alpha$_{2B}$ and/or alpha$_{2C}$ adrenergic agonists. Such conditions and diseases include, but are not limited to, pain including chronic pain (which may be, without limitation visceral, inflammatory, referred or neuropathic in origin) neuropathic pain, corneal pain, glaucoma, reducing elevated intraocular pressure, ischemic neuropathies and other neurodegenerative diseases, diarrhea, and nasal congestion. Chronic pain may arise as a result of, or be attendant to, conditions including without limitation: arthritis, (including rheumatoid arthritis), spondylitis, gouty arthritis, osteoarthritis, juvenile arthritis, and autoimmune diseases including without limitation, lupus erythematosus. Visceral pain may include, without limitation, pain caused by cancer or attendant to the treatment of cancer as, for example, by chemotherapy or radiation therapy. In addition, the compounds of this invention are useful for treating muscle spasticity including hyperactive micturition, diuresis, withdrawal syndromes, neurodegenerative diseases including optic neuropathy, spinal ischemia and stroke, memory and cognition deficits, attention deficit disorder, psychoses including manic disorders, anxiety, depression, hypertension, congestive heart failure, cardiac ischemia and nasal congestion, chronic gastrointestinal inflammations, Crohn's disease, gastritis, irritable bowel syndrome (IBS), functional dyspepsia and ulcerative colitis. The activity of the alpha$_{2B/2C}$ specific or selective compounds of the invention is highly advantageous because the administration of these compounds to mammals does not result in sedation or in significant cardiovascular effects (such as changes in blood pressure or heart rate).

The compounds of the invention act and can be used as a highly effective analgesic, particularly in chronic pain models, with minimal undesirable side effects, such as sedation and cardiovascular depression, commonly seen with other agonists of the alpha$_2$ receptors.

The compounds of the invention may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdemmal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

Another aspect of the invention is drawn to therapeutic compositions comprising the compounds of Formula 1 and pharmaceutically acceptable salts of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as a excipient or vehicle for the active compound. The formulations may also include wetting agents, emulsifying agents, preserving agents, sweetening agents, and/or flavoring agents. If used in an ophthalmic or infusion format, the formulation will usually contain one or more salts to influence the osmotic pressure of the formulation.

In another aspect, the invention is directed to methods for the treatment of pain, particularly chronic pain, through the administration of one or more compounds of Formula 1 or pharmaceutically acceptable salts thereof to a mammal in need thereof. As indicated above, the compound will usually be formulated in a form consistent with the desired mode of delivery.

It is known that chronic pain (such as pain from cancer, arthritis, and many neuropathic injuries) and acute pain (such as that pain produced by an immediate mechanical stimulus, such as tissue section, pinch, prick, or crush) are distinct neurological phenomena mediated to a large degree either by different nerve fibers and neuroreceptors or by a rearrangement or alteration of the function of these nerves upon chronic stimulation. Sensation of acute pain is transmitted quite quickly, primarily by afferent nerve fibers termed C fibers, which normally have a high threshold for mechanical, thermal, and chemical stimulation. While the mechanisms of chronic pain are not completely understood, acute tissue injury can give rise within minutes or hours after the initial stimulation to secondary symptoms, including a regional reduction in the magnitude of the stimulus necessary to elicit a pain response. This phenomenon, which typically occurs in a region emanating from (but larger than) the site of the original stimulus, is termed hyperalgesia. The secondary response can give rise to profoundly enhanced sensitivity to mechanical or thermal stimulus.

The A afferent fibers (Aβ and A* fibers) can be stimulated at a lower threshold than C fibers, and appear to be involved in the sensation of chronic pain. For example, under normal conditions, low threshold stimulation of these fibers (such as a light brush or tickling) is not painful. However, under certain conditions such as those following nerve injury or in the herpes virus-mediated condition known as shingles the application of even such a light touch or the brush of clothing can be very painful. This condition is termed allodynia and appears to be mediated at least in part by Aβ afferent nerves. C fibers may also be involved in the sensation of chronic pain, but if so it appears clear that persistent firing of the neurons over time brings about some sort of change which now results in the sensation of chronic pain.

By "acute pain" is meant immediate, usually high threshold, pain brought about by injury such as a cut, crush, burn, or by chemical stimulation such as that experienced upon exposure to capsaicin, the active ingredient in chili peppers.

By "chronic pain" is meant pain other than acute pain, such as, without limitation, neuropathic pain, visceral pain (including that brought about by Crohn's disease and irritable bowel syndrome (IBS)), and referred pain.

The following in vivo assays can be employed to demonstrate the biological activity of the compounds of the invention.

Sedative Activity

To test sedation, six male Sprague-Dawley rats are given up to 3 mg/kg of the test compound in a saline or DMSO vehicle by intraperitoneal injection (i.p.). Sedation is graded 30 minutes following administration of the drug by monitoring locomotor skills as follows.

The Sprague-Dawley rats are weighed and 1 ml/kg body weight of an appropriate concentration (ie. 3 mg/ml for a final dose of 3 mg/kg) drug solution is injected intraperitoneally. Typically the test compound is formulated in approximately 10 to 50% DMSO. The results are compared to controls that are injected with 1 ml/kg saline or 10 to 50% DMSO. Rat activity is then determined 30 minutes after injection of the drug solution. Rats are placed in a dark covered chamber and a digicom analyzer (Omnitech Electronic) quantitates their exploratory behavior for a five-minute period. The machine records each time the rat interrupts an array of 32 photoelectric beams in the X and Y orientation. Representative Compounds 7 and 15 of the invention were tested in this assay intraperitoneally and up to a dose of 1 mg/kg, and were found to have no sedative effect. The results in this test with other compounds of the invention are also expected to show that the compounds of the invention have no significant sedatory activity.

Effects on Cardiovascular System

To test the effect of the compounds on the cardiovascular system, typically six cynomolgus monkeys are given 500 μg/kg of the test compound by intravenous injection (i.v.) Or 3 mg/kg by oral gavage. The effects of the compound on the animals' blood pressure and heart rate is measured at time intervals from 30 minutes to six hours following administration of the drug. The peak change from a baseline measurement taken 30 minutes before drug administration is recorded using a blood pressure cuff modified for use on monkeys.

Specifically and typically the monkeys are weighed (approximately 4 kg) and an appropriate volume (0.1 ml/kg) of a 5 mg/ml solution of the test compound formulated in 10 to 50% DMSO is injected into the cephalic vein in the animals' arm. Cardiovascular measurements are made with a BP 100S automated sphygmomanometer (Nippon Colin, Japan) at 0.5, 1, 2, 4 and 6 hours.

The results of this test are expected to show that the compounds of the invention have no or only minimal detectable effect on the cardiovascular system.

Alleviation of Acute Pain

Models to measure sensitivity to acute pain have typically involved the acute application of thermal stimuli; such a stimulus causes a programmed escape mechanism to remove the affected area from the stimulus. The proper stimulus is thought to involve the activation of high threshold thermoreceptors and C fiber dorsal root ganglion neurons that transmit the pain signal to the spinal cord.

The escape response may be "wired" to occur solely through spinal neurons, which receive the afferent input from the stimulated nerve receptors and cause the "escape" neuromuscular response, or may be processed supraspinally—that is, at the level of the brain. A commonly used method to measure nociceptive reflexes involves quantification of the withdrawal or licking of the rodent paw following thermal excitation. See Dirig, D. M. et al., *J. Neurosci. Methods* 76:183-191 (1997) and Hargreaves, K. et al., *Pain* 32:77-88 (1988), hereby incorporated by reference herein.

In a variation of this latter model, male Sprague-Dawley rats are tested by being placed on a commercially available thermal stimulus device constructed as described in Hargreaves et al. This device consists of a box containing a glass plate. The nociceptive stimulus is provided by a focused projection bulb that is movable, permitting the stimulus to be applied to the heel of one or both hindpaws of the test animal. A timer is actuated with the light source, and the response latency (defined as the time period between application of the stimulus and an abrupt withdrawal of the hindpaw) is registered by use of a photodiode motion sensor array that turns off the timer and light. Stimulus strength can be controlled by current regulation to the light source. Heating is automatically terminated after 20 seconds to prevent tissue damage.

Typically four test animals per group are weighed (approximately 0.3 kg) and injected intraperitonealy (i.p.) with 1 ml/kg of the test compound formulated in approximately 10 to 50% dimethylsulfoxide (DMSO) vehicle. Animals typically receive a 0.1 mg/kg and a 1 mg/kg dose of the three compounds. Rats are acclimated to the test chamber for about 15 minutes prior to testing. The paw withdrawal latency is measured at 30, 60 and 120 minutes after drug administration. The right and left paws are tested 1 minute apart, and the response latencies for each paw are averaged. Stimulus intensity is sufficient to provide a temperature of 45-50 degrees centigrade to each rat hindpaw.

Alleviation of Chronic Pain

A model in accordance with *Kim and Chung* 1992, Pain 150, pp 355-363 (Chung model), for chronic pain (in particular peripheral neuropathy) involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to pain from low-threshold mechanical stimuli, such as that producing a faint sensation of touch in a human, within about 1 week following surgery. This sensitivity to normally non-painful touch is called "tactile allodynia" and lasts for at least two months. The response includes lifting the affected hindpaw to escape from the stimulus, licking the paw and holding it in the air for many seconds. None of these responses is normally seen in the control group.

Rats are anesthetized before surgery. The surgical site is shaved and prepared either with betadine or Novocaine. Incision is made from the thoracic vertebra XIII down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

A complete hemostasis is confirmed, then the wounds are sutured. A small amount of antibiotic ointment is applied to the incised area, and the rat is transferred to the recovery plastic cage under a regulated heat-temperature lamp. On the day of the experiment, at least seven days after the surgery, typically six rats per test group are administered the test drugs by intraperitoneal (i.p.) injection or oral gavage. For i.p. injection, the compounds are formulated in d $H_2O$ and given in a volume of 1 ml/kg body weight using an 18-gauge, 3 inch gavage needle that is slowly inserted through the esophagus into the stomach.

Tactile allodynia is measured prior to and 30 minutes after drug administration using von Frey hairs that are a series of fine hairs with incremental differences in stiffness. Rats are placed in a plastic cage with a wire mesh bottom and allowed to acclimate for approximately 30 minutes. The von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol. Toxicol.* 20:441-462 (1980) hereby incorporated by reference. The post-drug threshold is compared to the pre-drug threshold and the percent reversal of tactile sensitivity is calculated based on a normal threshold of 15.1 grams.

TABLE 2

| Activity of the Compounds of the Invention in the Chung Model of Neuropathic Pain (% Pain Reversal ± SEM) | | | |
|---|---|---|---|
| Dose and Route of Administration of Compound 7 | | | |
| Compd. | 10 µg/kg i.p. | 30 µg/kg i.p. | 300 µg/kg i.p. |
| 7 | 2.9 ± 0.7 | 65.8 ± 6.1 | 77.7 ± 7.2 |
| Dose and Route of Administration of Compounds 7 and 15 | | | |
| Compd. | 3 µg/kg p.o. | 10 µg/kg p.o. | 30 µg/kg p.o. | 100 µg/kg p.o.. |
| 7 | | | 77.0 ± 5.1 | |
| 15 | 58.0 ± 5.3 | 78.0 ± 4.6 | 82.0 ± 6.2 | 81.0 ± 8.1 |

All measurements 30 min following drug administration.

p value <0.001 compared to pretreatment values.

The results shown in Table 2 illustrate that these compounds of the invention significantly alleviate allodynic pain, and based on these test and/or on the compounds ability to activate $alpha_{2B}$ and/or $alpha_{2C}$ adrenergic receptors in preference over $alpha_{2A}$ adrenergic receptors, the compounds of the invention are expected to be useful as analgesics to alleviate allodynia and chronic pain.

The Mouse Sulprostone Model is an alternative model in which chronic pain, allodynia can be induced in mice through intrathecal treatment of the animals with 200 ng sulprostone (prostaglandin E2 receptor agonist) in 50% DMSO and in volume of 5 µl. In this model, the pain response to stroking the flank with a paint brush is scored 8 times over a 35 minute period starting 15 minutes following final administration of sulprostone. Minami et al., 57 Pain 217-223 (1994), hereby incorporated by reference. Sulprostone treatment alone elicits a score of 12-13 on a 16-point scale.

In variants of this model, allodynia can be induced using intraperitoneal injection of 300 µg/kg sulprostone or 30 µg/kg phenylephrine. Alternatively allodynia can be induced using intrathecal injection of 100 ng N-methyl-D-aspirate (NMDA) or 30 ng phenylephrine (PE) formulated in $dH_2O$ in a volume of e.g. 5 microliters.

In either model, the compounds are formulated in $dH_2O$ and given in a volume of 1 ml/kg body weight for intraperitoneal (IP) dosing.

Specific Embodiments, Experimental

Example A

Method A: Procedure for the preparation of 4-(2,3-dihydro-benzo[1,4]dioxin-5-ylmethyl)-1,3-dihydro-imidazole-2-thione (Compound 1)

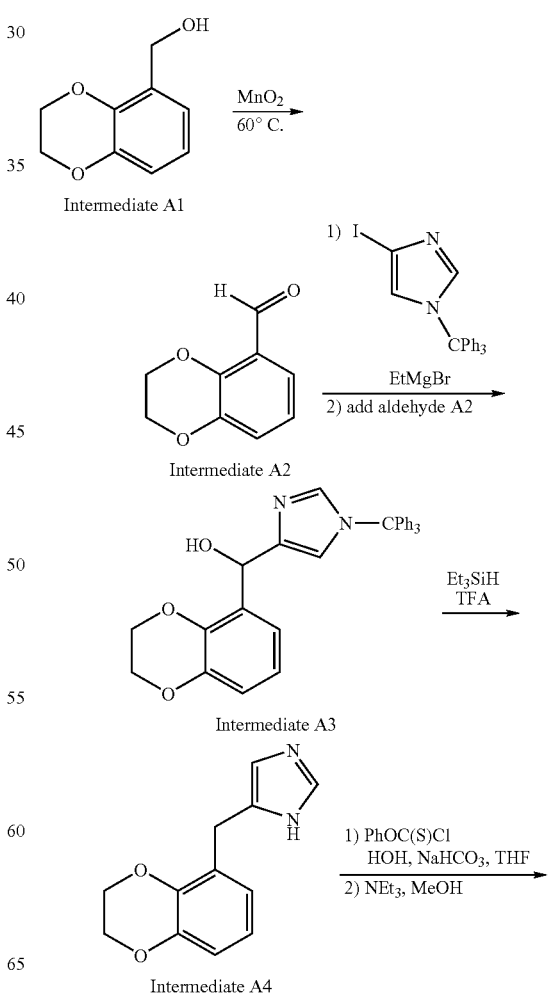

-continued

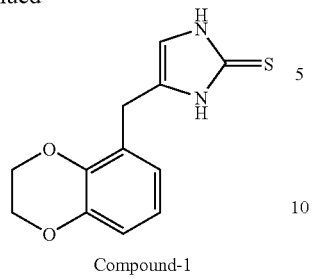

Compound-1

A solution of 2,3-dihydro-1,4-benzodioxin-5-ylmethanol (Intermediate A1) (commercially available from Aldrich) (3 g, 18.1 mmol) in THF (100 mL) was treated with manganese (IV) oxide, activated (commercially available from Aldrich): $MnO_2$ (10 g, 115 mmol) at rt. The mixture was heated to 35° C. for 2 h and 60° C. for 4 h followed by 18 h at room temperature (rt). The mixture was filtered through celite and the solvent was removed under vacuum. The residue was purified by chromatography on silica gel with 20% EtOAc: hexanes to give 2,3-dihydro-benzo[1,4]dioxine-5-carbaldehyde (Intermediate A2) 2.6 g (88%).

A mixture of 4-iodo-1-tritylimidazole (commercially available) (8.64 g, 19.8 mmol) in dichloromethane (100 mL) at −10° C. was treated with ethyl magnesium bromide (6.3 mL, 19 mmol, 3M in THF) and allowed to react for 45 m. A solution of 2,3-dihydro-benzo[1,4]dioxine-5-carbaldehyde (Intermediate A2) (2.6 g, 15.9 mmol) in dichloromethane was added via syringe at −10° C. and stirred for 45 m. The mixture was quenched with water (50 mL) and a sat. solution of ammonium chloride (50 mL). The residue was isolated in a typical aqueous workup and purified by chromatography on silica gel with 3 to 5% $NH_3$-MeOH:$CH_2Cl_2$ to give (2,3-dihydro-benzo[1,4]dioxin-5-yl)-(1-trityl-1H-imidazol-4-yl)-methanol (Intermediate A3) as a solid, 2.9 g (40%).

A solution of (2,3-dihydro-benzo[1,4]dioxin-5-yl)-(1-trityl-1H-imidazol-4-yl)-methanol (Intermediate A3) (1 g, 2.11 mmol) in dichloromethane (30 mL) was reacted with TFA: trifluoroacetic acid (5.3 mL, 68 mmol)) and triethylsilane (TES) (2.8 mL, 17 mmol) at rt for 24 h. The mixture was evaporated under reduced pressure and quenched with solid $NaHCO_3$. This material was subjected to an aqueous work-up and the residue was purified by chromatography on silica gel with 5% $NH_3$-MeOH:$CH_2Cl_2$ to yield 5-(2,3-dihydro-benzo[1,4]dioxin-5-ylmethyl)-1H-imidazole (Intermediate A4) 330 mg (72%).

A mixture of 5-(2,3-dihydro-benzo[1,4]dioxin-5-ylmethyl)-1H-imidazole (Intermediate A4) (260 mg, 1.2 mmol) in THF (10 mL) and water (10 mL) was treated with $NaHCO_3$ (1 g, 12 mmol) and phenylchlorothionoformate (0.42 mL, 3.13 mmol) for 3 h at rt. The mixture was diluted with diethyl ether (35 mL) and water (10 mL). The aqueous layer was removed and extracted with ether (2×10 mL). The organic layers were combined, dried over $MgSO_4$, filtered and concentrated under vacuum. The residue was treated with triethylamine (1 mL) in methanol (9 mL) at rt for 16 h. The solvent was removed and the product was isolated and purified either by tituration with $CH_2Cl_2$: hexane or by chromatography on $SiO_2$ with EtOAc or 3% MeOH:$CH_2Cl_2$. This gave 4-(2,3-dihydro-benzo[1,4]dioxin-5-ylmethyl)-1,3-dihydro-imidazole-2-thione (Compound-1) 150 mg (50%).

$^1$H NMR (300 MHz, DMSO-$d^6$ w/TMS): δ 11.9 (brs, 1H), 11.7 (s, 1H), 6.76-6.65 (m, 3H), 6.41 (s, 1H), 4.28-4.21 (m, 4H), 3.61 (s, 2H).

Example B

Method B Procedure for the preparation of 4-[1-(2,3-dihydro-benzo[1,4]dioxin-5-yl)-ethyl]-1,3-dihydro-imidazole-2-thione (Compound-2)

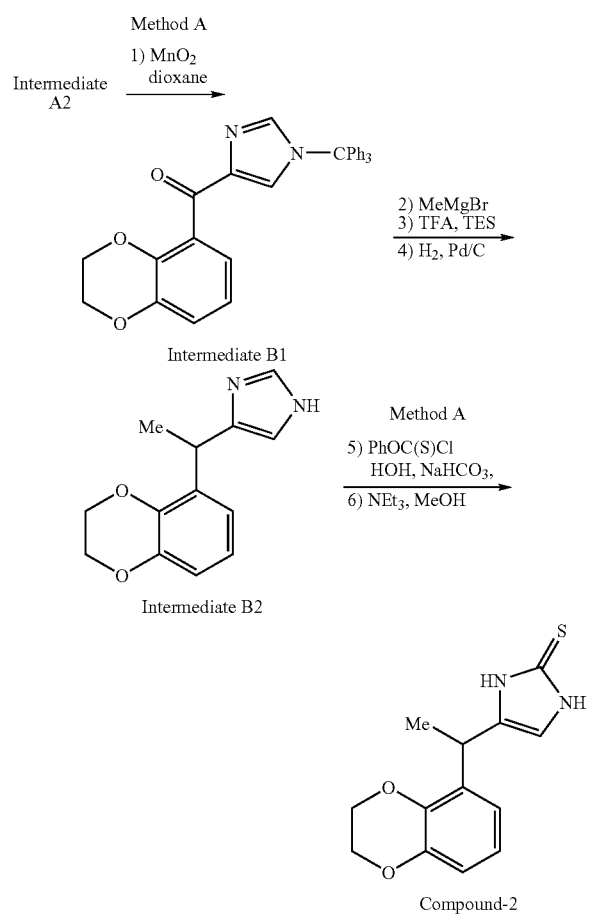

2,3-Dihydro-benzo[1,4]dioxine-5-carbaldehyde (Intermediate A2) was oxidized by manganese dioxide (in accordance with the applicable step of Method A) to give (2,3-dihydro-benzo[1,4]dioxin-5-yl)-(1-trityl-1H-imidazol-4-yl)-methanone (Intermediate B1) (83%).

A solution of (2,3-dihydro-benzo[1,4]dioxin-5-yl)-(1-trityl-1H-imidazol-4-yl)-methanone (Intermediate B1) (0.91 g, 1.93 mmol) in THF (80 mL) at −10° C. was treated with MeMgBr (2.6 mL, 7.68 mmol of a 3M solution in $Et_2O$) for 45 m. The mixture was quenched with a sat. solution of $NH_4Cl$ and water. The layers were separated and the organic layer dried over $MgSO_4$. The suspension was filtered and evaporated to dryness. The material was purified by chromatography on $SiO_2$ with 50% EtOAc in $CHCl_3$ to give 1-(2,3-dihydro-benzo[1,4]dioxin-5-yl)-1-(1-trityl-1H-imidazol-4-yl)-ethanol as a foam 0.95 g (98%).

A solution of 1-(2,3-dihydro-benzo[1,4]dioxin-5-yl)-1-(1-trityl-1H-imidazol-4-yl)-ethanol (0.95 g) in dichloromethane (10 mL) was treated with trifluoroacetic acid (6 mL) and triethylsilane (4 mL) at rt for 24 h. The reaction mixture was quenched with solid $NaHCO_3$ and subjected to an aqueous work-up. The residue was purified by chromatography on silica gel with 4% $NH_3$-MeOH: $CH_2Cl_2$ to give a mixture of two products: 4-[1-(2,3-dihydro-benzo[1,4]dioxin-5-yl)-ethyl]-1H-imidazole and 4-[1-(2,3-dihydro-benzo[1,4]dioxin-5-yl)-vinyl]-1H-imidazole.

A mixture of 4-[1-(2,3-dihydro-benzo[1,4]dioxin-5-yl)-ethyl]-1H-imidazole and 4-[1-(2,3-dihydro-benzo[1,4]dioxin-5-yl)-vinyl]-1H-imidazole (350 mg) in EtOH (35 mL) was reduced by the action of 10% Pd/C (100 mg) under H₂ at 35 psi for 12 h at rt. The mixture was filtered through Celite and freed of solvent under reduced pressure. The residue was purified by chromatography on silica gel with 5% NH₃-MeOH: CH₂Cl₂ to give 4-[1-(2,3-dihydro-benzo[1,4]dioxin-5-yl)-ethyl]-1H-imidazole (Intermediate-B2) as a solid, 280 mg (80%).

4-[1-(2,3-dihydro-benzo[1,4]dioxin-5-yl)-ethyl]-1H-imidazole (Intermediate-B2) (250 mg, 1.09 mmol) was subjected to the applicable steps of Method A to produce 4-[1-(2,3-dihydro-benzo[1,4]dioxin-5-yl)-ethyl]-1,3-dihydro-imidazole-2-thione (Compound-2) as a white solid, 80 mg (35%).

$^1$H NMR (300 MHz, DMSO-d$^6$ w/TMS): δ 11.9 (brs, 1H), 11.7 (s, 1H), 6.77-6.58 (m, 3H), 6.46 (s, 1H), 4.28-4.18 (m, 5H), 1.38 (d, J=6.9 Hz, 3H).

Example B-1

Compound-3

Use of 2,3-(methylenedioxy)benzaldehyde (commercially available from Aldrich) in Method B produced 4-(1-benzo[1,3]dioxol-4-yl-ethyl)-1,3-dihydro-imidazole-2-thione (Compound-3).

$^1$H NMR (300 MHz, methanol-d$^4$): δ 6.79-6.60 (m, 3H), 6.54 (d, J=1.2 Hz, 1H), 5.92 (s, 2H), 4.09 (q, J=6.6 Hz, 1H), 1.52 (d, 7.2 Hz, 3H).

Example C

Method C: Procedure for the preparation of 4-(1-quinolin-8-yl-ethyl)-1,3-dihydro-imidazole-2-thione (Compound 4)

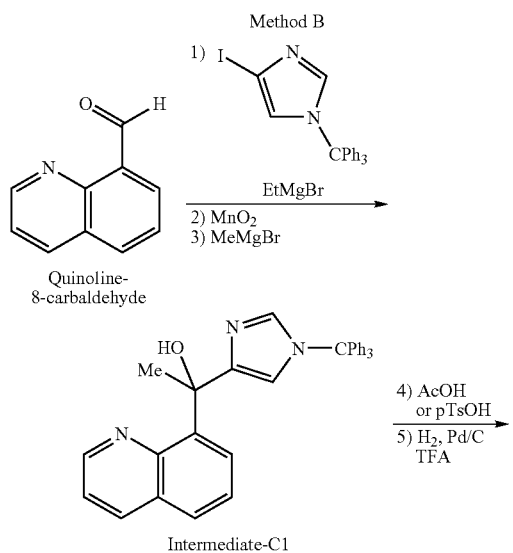

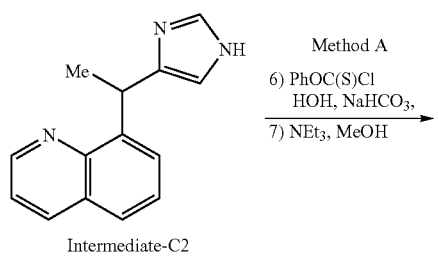

Intermediate-C2

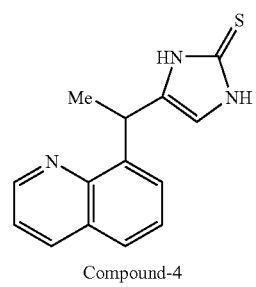

Compound-4

Quinoline-8-carbaldehyde (commercially available from Lancaster) was subjected to the applicable process steps in Method B to produce 1-quinolin-8-yl-1-(1-trityl-1H-imidazol-4-yl)-ethanol (Intermediate C1).

1-Quinolin-8-yl-1-(1-trityl-1H-imidazol-4-yl)-ethanol (Intermediate C1) and p-toluenesulfonic acid catalyst in toluene was heated to reflux in a Dean-Stark apparatus for 18 h. The mixture was cooled to rt and freed of solvent. The residue was dissolved in 70% acetic acid:water and heated to 100° C. for 1 h. The reaction mixture was cooled to rt and basified with 2 M NaOH and extracted with chloroform: isopropyl alcohol (3:1). The organic layers were pooled, dried over MgSO₄, filtered and concentrated onto silica gel. The product was eluted from a column of silica gel with 4% NH₃-MeOH: CH₂Cl₂ to give 8-[1-(1H-imidazol-4-yl)-vinyl]-quinoline.

The vinyl compound, 8-[1-(1H-imidazol-4-yl)-vinyl]-quinoline (0.23 g) in trifluoroacetic acid: TFA (15 mL) was reduced by the action of 10% Pd/C (58 mg) under 50 psi of hydrogen for 18 h at rt. The mixture was filtered through Celite and basified with NH₃-MeOH. The solvent was removed under vacuum. The residue was purified by chromatography on silica gel with 4% NH₃-MeOH: CH₂Cl₂ to give 8-[1-(1H-imidazol-4-yl)-ethyl]-quinoline (Intermediate C2) 0.2 g.

8-[1-(1H-Imidazol-4-yl)-ethyl]-quinoline (Intermediate C2) was subjected to the appropriate process steps in Method A to produce 4-(1-quinolin-8-yl-ethyl)-1,3-dihydro-imidazole-2-thione (Compound-4).

$^1$H NMR (300 MHz, methanol-d$^4$): δ 8.93-8.91 (m, 1H), 8.33-8.30 (m, 1H), 7.83-7.80 (m, 1H), 7.56-7.48 (m, 3H), 6.65 (s, 1H), 5.40 (q, J=9 Hz, 1H), 1.64 (d, J=6 Hz, 3H).

Example D

Method D: Procedure for the preparation of 4-benzo[1,3]dioxol-5-ylmethyl-1,3-dihydro-imidazole-2-thione (Compound-5)

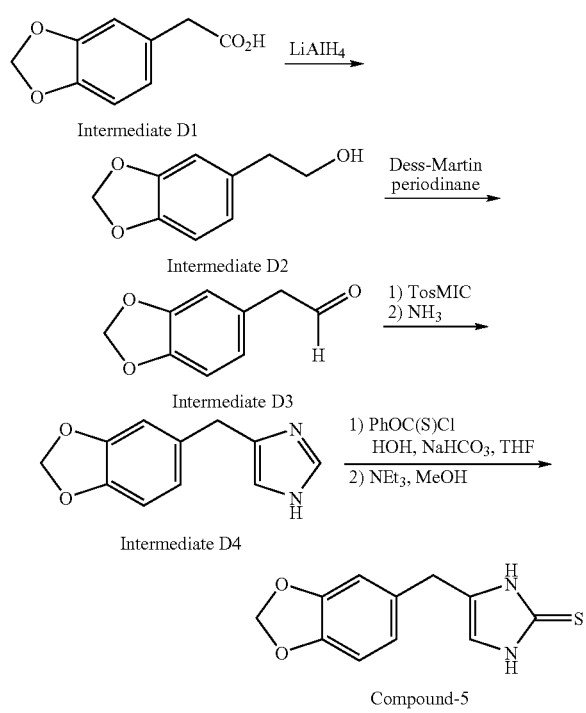

Compound-5

A solution of 3,4-(methylenedioxy)phenylacetic acid (Intermediate D1) (commercially available from Aldrich) (2 g, 11 mmol) in diethyl ether (40 mL) and THF (60 mL) was treated with lithium aluminum hydride: LiAlH$_4$ (24 mL, 1 M in ether) at rt for 16 h. Rochelle's salt solution was added to quench the reaction mixture. The aqueous layer was extracted with ether (3×100 mL). The combined organic fractions were dried over MgSO$_4$, filtered and evaporated to give 1.8 g of 2-benzo[1,3]dioxol-5-yl-ethanol (Intermediate D2) that was sufficiently pure to be used in the next synthetic step.

A solution of 2-benzo[1,3]dioxol-5-yl-ethanol (Intermediate D2) (1 g, 6.0 mmol) in dichloromethane (40 mL) was treated with the Dess-Martin periodinane (commercially available from Lancaster) (2.65 g, 6.25 mmol) at rt for 2 h. Silica gel was added to the mixture and the solvent was removed under vacuum. The solids were placed onto a column of silica gel and the product was eluted with a mixture of ether: hexanes to give benzo[1,3]dioxol-5-yl-acetaldehyde (Intermediate D3) 0.75 g.

This preparation of Intermediate D4 followed the procedure by Horne, D. A.; Yakushijin, K.; Büchi, G. *Heterocycles*, 1994, 39, 139 ("Büchi protocol") incorporated herein by reference. A solution of benzo[1,3]dioxol-5-yl-acetaldehyde (Intermediate D3) (0.75 g, 4.57 mmol) in EtOH (10 mL) was treated with tosylmethyl isocyanide (TosMIC) (0.87 g, 4.45 mmol) and NaCN (~15 mg, cat.). This mixture was allowed to stir at rt for 20 m. The solvent was removed in vacuo and the residue was dissolved in ~7M NH$_3$ in MeOH (45 mL) and transferred to a resealable tube. This mixture was heated to at 90-100° C. for 12 h. The mixture was concentrated and purified by chromatography on SiO$_2$ with 5% MeOH (sat. w/NH$_3$):CH$_2$Cl$_2$ to give 4-benzo[1,3]dioxol-5-ylmethyl-1H-imidazole (Intermediate D4) 0.4 g (43%) as an amber oil.

A solution of 4-benzo[1,3]dioxol-5-ylmethyl-1H-imidazole (Intermediate D4) (0.24 g, 1.18 mmol) in THF (4 mL) and water (4 mL) was treated with NaHCO$_3$ (1 g, 11.9 mmol) at rt for 10 m. Phenyl chlorothionoformate (0.42 mL, 3.1 mmol) was added and stirring was continued for 3 h. The mixture was diluted with water (10 mL) and extracted with ether (3×15 mL). The organic portions were combined, dried over MgSO$_4$, filtered and freed of solvent. The residue was dissolved in MeOH (8 mL) and treated with NEt$_3$ (1 mL) for 16 h. The solvent was removed under vacuum and the product was washed on a glass frit with 50% CH$_2$Cl$_2$:hexanes to give a white solid (~36%) 4-benzo[1,3]dioxol-5-ylmethyl-1,3-dihydro-imidazole-2-thione (Compound 5)

$^1$H NMR (300 MHz, DMSO-d$^6$ w/TMS): δ 11.9 (brs, 1H), 11.6 (br s, 1H), 6.84-6.82 (m, 2H), 6.72-6.71 (m, 1H), 6.52 (s, 1H), 5.95 (s, 2H), 3.58 (s, 2H).

Example D-1

Use of 1-naphthalene ethanol (commercially available from Aldrich) in Method D produced 4-naphthalen-1-ylmethyl-1,3-dihydro-imidazole-2-thione (Compound-6).

$^1$H NMR (500 MHz, DMSO-d$^6$ w/TMS): δ 12.02 (brs, 1H), 11.70 (s, 1H), 8.10 (d, J=4.8 Hz, 1H), 7.94 (d, J=4.2 Hz, 1H), 7.83 (d, J=5.1 Hz, 1H), 7.54-7.52 (m, 1H), 7.46 (t, J=4.2 Hz, 1H), 7.38 (d, J=4.2 Hz, 1H), 6.48 (s, 1H), 4.17 (s, 2H).

Example E

Method E: Procedure for the Preparation of 4-(1-quinolin-5-yl-ethyl)-1,3-dihydro-imidazole-2-thione (Compound 7)

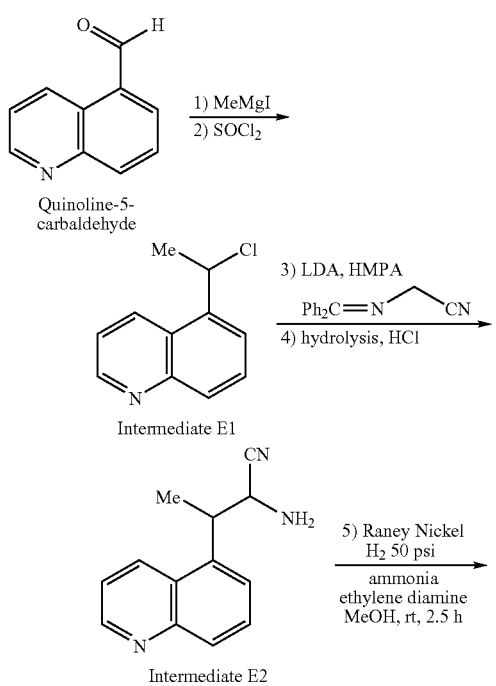

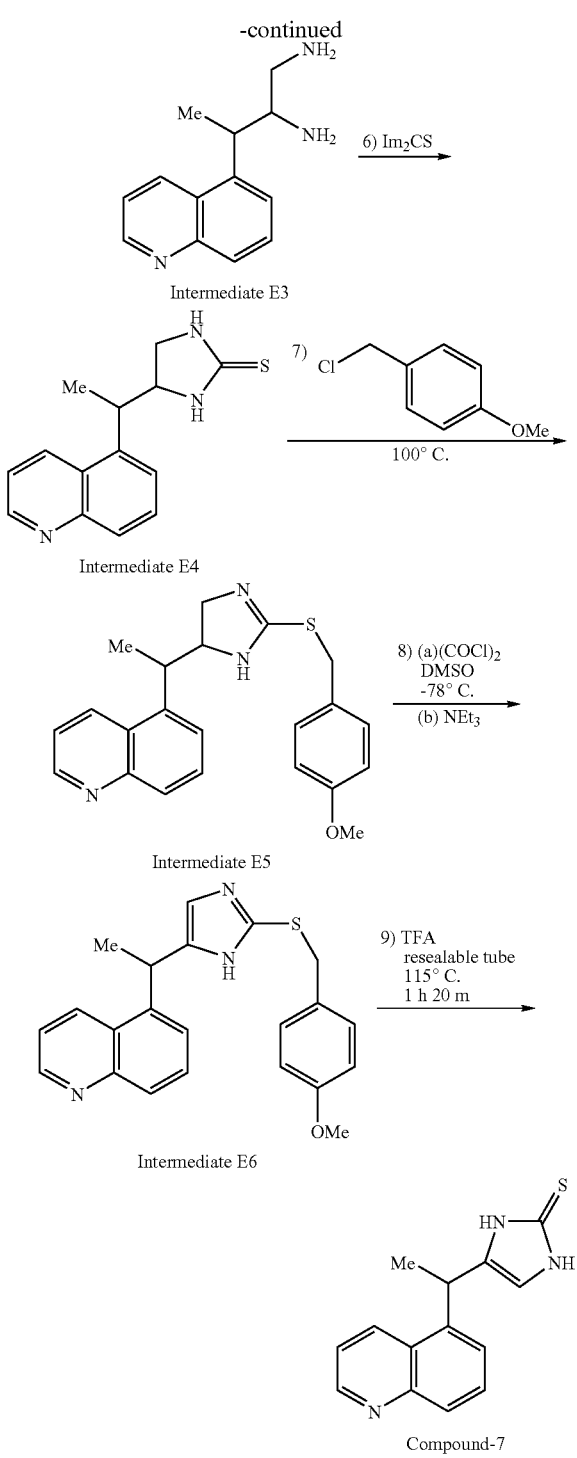

The alcohol, 1-quinolin-5-yl-ethanol (5.0 g, 28.9 mmol) in chloroform was treated with a dropwise addition of thionyl chloride (5.26 mL, 72.1 mmol) at rt. After 1 h the mixture was cooled to 0° C. and carefully quenched with a sat. solution of NaHCO$_3$ followed by 2M NaOH until the pH was >8. The aqueous layer was extracted with chloroform and the organic fractions were combined, dried over MgSO$_4$, filtered, and freed of solvent. The residue was purified by chromatography on SiO$_2$ eluting with 30% ethyl acetate:hexane. The product, 5-(1-chloro-ethyl)-quinoline (Intermediate E1) was obtained as a clear oil, 4.22 g (76%).

A solution of N-(diphenylmethylene)aminoacetonitrile (5.84 g, 26.0 mmol, commercially available from Aldrich) in THF (20 mL) and hexamethylphosphoramide (HMPA) (5.43 mL, 31 mmol) at −78° C. was reacted with lithium diisopropylamide (LDA) (15.4 mL of a 2M soln in heptane/THF/ethylbenzene) (commercially available from Aldrich). After 1 h, 5-(1-chloro-ethyl)-quinoline (Intermediate E1) (4.15 g, 21.7 mmol) in THF (15 mL) was introduced by dropwise addition. The mixture was kept at −78° C. for 5 m before removal of the cold bath. After 5 m, the mixture was quenched with cold water and extracted with ethyl acetate (3×). The organic solution was dried over MgSO$_4$, filtered and concentrated to give 2-(benzhydrylidene-amino)-3-quinolin-5-yl-butyronitrile that was used in the next step without further purification.

2-(Benzhydrylidene-amino)-3-quinolin-5-yl-butyronitrile (8.36 g, 22.3 mmol) in dioxane (90 mL) was hydrolyzed with 1M HCl (90 mL) and the solution was stirred at rt for 16 h. The dioxane was removed under vacuum and the mixture was made basic with 2 M NaOH. The aqueous solution was extracted with chloroform:isopropanol (3:1). The organic extracts were pooled, dried over MgSO$_4$, filtered and evaporated to leave an oil. The oily residue was purified by chromatography on SiO$_2$, eluting with ethyl acetate and 5% methanol:ethyl acetate to give 2-amino-3-quinolin-5-yl-butyronitrile (Intermediate-E2) as a yellow solid 3.61 g (77%).

In a Parr bottle, a mixture of 2-amino-3-quinolin-5-yl-butyronitrile (Intermediate-E2) (5.38 g, 25.4 mmol) in MeOH (100 mL) and ethylene diamine (3.2 mL, 47.8 mmol) was reacted with Raney 2800 nickel (18.9 g) and bubbled with ammonia gas for 10 m. The Parr bottle was pressurized with hydrogen at 50 psi and shaken on a Parr apparatus for 2.5 h at rt. The mixture was filtered through celite, washed with MeOH (3×) and evaporated to leave a residue. This material was placed onto a column and eluted with a gradient of 1% to 5% sat. NH$_3$-MeOH:CH$_2$Cl$_2$ to give 3-quinolin-5-yl-butane-1,2-diamine (Intermediate E3) 3.9 g (71%).

3-Quinolin-5-yl-butane-1,2-diamine (Intermediate E3) (1.8 g, 8.35 mmol) in CH$_2$Cl$_2$ (20 mL) was treated with a solution of 1,1'-thiocarbonyldiimidazole (1.52 g, 8.54 mmol) in CH$_2$Cl$_2$ (40 mL) at 0° C. for 1 h. The mixture was diluted with chloroform (40 mL) and water (60 mL). The aqueous layer was extracted with chloroform (3×30 mL) and CH$_2$Cl$_2$ (6×30 mL). The organic solution was dried over MgSO$_4$, filtered and evaporated to give a residue. The material was purified by chromatography on SiO$_2$ with 3% NH$_3$-MeOH:CH$_2$Cl$_2$ to give 4-(1-quinolin-5-yl-ethyl)-imidazolidine-2-thione (Intermediate E4) 2 g (93%).

A mixture of 4-(1-quinolin-5-yl-ethyl)-imidazolidine-2-thione (Intermediate E4) (4.0 g, 15.5 mmol) in ethanol (120 mL) was treated with p-methoxybenzylchloride (4.22 mL, 27 mmol). The solution was heated in an oil bath (bath temp. 100° C.) for 1 h. The solvent was removed under vacuum and replaced with 10% NaOH (160 mL). The aqueous mixture was extracted with CH$_2$Cl$_2$ (2×100 mL) and chloroform (2×100 mL). The organic solution was dried over MgSO$_4$, filtered, evaporated and purified by chromatography on SiO$_2$ eluting with 2 to 4% NH$_3$-MeOH:CH$_2$Cl$_2$. The product was 5-{1-[2-(4-methoxy-benzylsulfanyl)-4,5-dihydro-3H-imidazol-4-yl]-ethyl}-quinoline (Intermediate E5) 4.16 g (71%).

A Swern-type reagent was formed in standard fashion: oxalyl chloride (9.15 mL as a 2M soln. in CH$_2$Cl$_2$) in CH$_2$Cl$_2$ (23 mL) was cooled to −78° C. and treated with a solution of DMSO (2.85 mL, 36.8 mmol) in CH$_2$Cl$_2$ (23 mL) for 30 m. To this solution was added 5-{1-[2-(4-methoxy-benzylsulfanyl)-4,5-dihydro-3H-imidazol-4-yl]-ethyl}-quinoline (Intermediate E5) (4.7 g, 12.4 mmol) in CH$_2$Cl$_2$ (30 mL) and stirring continued for 45 m at −78° C. Triethylamine (9 mL) was added at −78° C. and warmed to rt for 40 m. The reaction mixture was diluted with brine and CH$_2$Cl$_2$. The aqueous layer was extracted with ethyl acetate. The organic solution was dried over MgSO$_4$, filtered and evaporated to dryness. Chromatography on SiO$_2$ with 80 to 100% ethyl acetate:hexanes yielded 5-{1-[2-(4-methoxy-benzylsulfanyl)-3H-imidazol-4-yl]-ethyl}-quinoline (Intermediate E6) 3.45 g (74%).

5-{1-[2-(4-Methoxy-benzylsulfanyl)-3H-imidazol-4-yl]-ethyl}-quinoline (Intermediate E6) (3 g, 8.0 mmol) and trifluoroacetic acid (100 mL) in a resealable tube was heated to 115° C. for 1 h 20 m. The mixture was cooled to rt and TFA removed under vacuum. The residual acid was quenched with NH$_3$-MeOH. The residue was evaporated and resolvated with 3:1 chloroform:isopropanol (500 mL). The organic solution was washed with water (3×40 mL) and brine (1×30 mL). The solution was dried over MgSO$_4$, filtered, and evaporated to leave a solid. This material was purified on a short column of silica gel by gradient elution with 3 to 9% NH$_3$-MeOH:CH$_2$Cl$_2$ to give 4-(1-quinolin-5-yl-ethyl)-1,3-dihydro-imidazole-2-thione (Compound 7) 1.44 g (71%).

$^1$H NMR (300 MHz, methanol-d$^4$): δ 8.85 (dd, J=4.2, 1.5 Hz, 1H), 8.67 (d, J=8.4 Hz, 1H), 7.95 (d, J=9.0 Hz, 1H), 7.73 (dd, J=8.4, 7.2 Hz, 1H), 7.58 (dd, J=8.7, 4.5 Hz, 1H), 7.42 (d, J=6.6 Hz, 1H), 6.62 (s, 1H), 4.80-4.85 (m, 1H), 1.67 (d, J=7.2 Hz, 3H).

Continuation of Method E: Procedure for the Preparative Chiral HPLC Separation of Racemic (Compound 7) to provide (−)-4-(1-quinolin-5-yl-ethyl)-1,3-dihydro-imidazole-2-thione (Compound 14) and (+)-4-(1-quinolin-5-yl-ethyl)-1,3-dihydro-imidazole-2-thione (Compound 15)

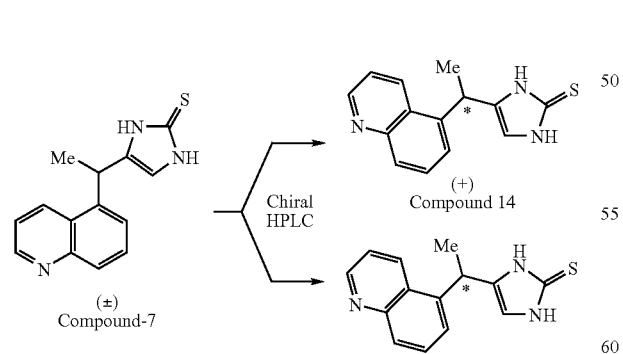

The racemate, 4-(1-quinolin-5-yl-ethyl)-1,3-dihydro-imidazole-2-thione (Compound 7) (~1.9 g) was separated by preparative Chiral HPLC with a CHIRALCEL-ODH column (available from Chiral Technologies, Inc.) eluent CO$_2$/MeOH: 80/20 at rt, 2 mL/min flow rate and 280 nm. The first eluting fraction was obtained after 8.6 m to give 0.61 g of (+)-4-(1-quinolin-5-yl-ethyl)-1,3-dihydro-imidazole-2-thione (Compound 14) $[\alpha]_{20}^D$ +101.5° (c=1.16 in DMSO). The second eluting fraction was obtained after 10.9 min to give 0.67 g of (−)-4-(1-quinolin-5-yl-ethyl)-1,3-dihydro-imidazole-2-thione (Compound 15) $[\forall]_{20}^D$ −110° (c=0.54 in DMSO).

Example F

Method F: Procedure for the preparation of 4-quinolin-8-ylmethyl-1,3-dihydro-imidazole-2-thione (Compound-8)

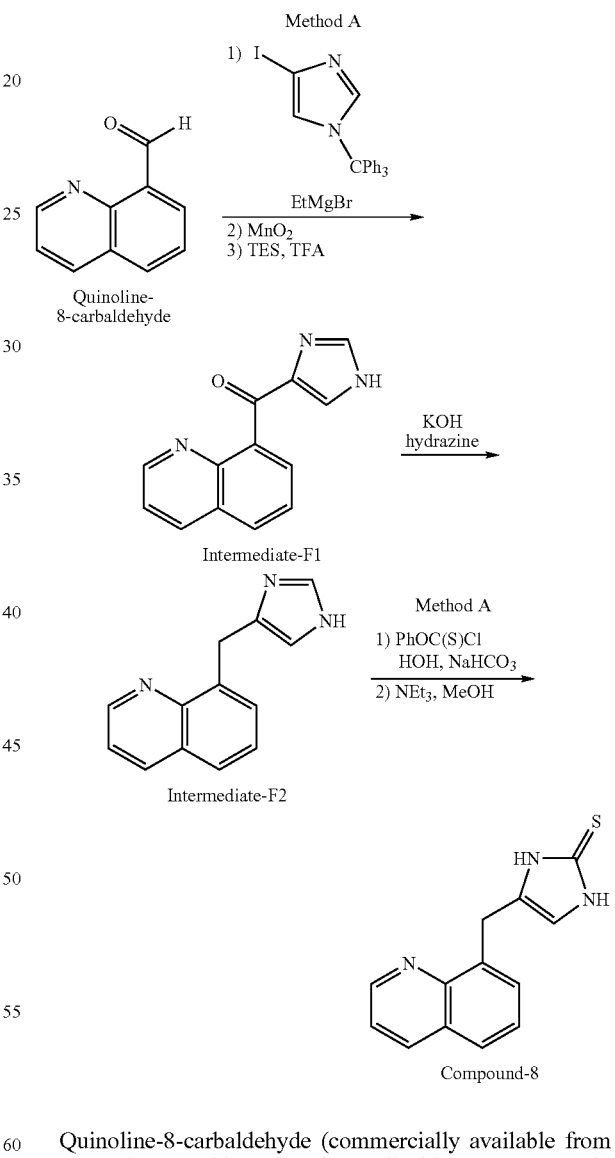

Quinoline-8-carbaldehyde (commercially available from Lancaster) was subjected to the applicable process steps in Method A to produce (1H-imidazol-4-yl)-quinolin-8-yl-methanone (Intermediate F1).

1(1H-imidazol-4-yl)-quinolin-8-yl-methanone (Intermediate F1) (0.85 g, 3.81 mmol) and KOH (0.86 g, 15.3 mmol) in ethylene glycol (15 mL) was treated with hydrazine hydrate (~1.5 mL) and heated to 120° C. for 4-6 h followed by heating to 180° C. for 6 h. The mixture was cooled to rt, diluted with brine, and extracted with chloroform:isopropanol (3:1). The organic solution was concentrated under vacuum. The residue was purified by chromatography on silica gel, eluting with 3% $NH_3$-MeOH: $CH_2Cl_2$ to give 8-(1H-imidazol-4-ylmethyl)-quinoline (Intermediate F2) as an oil.

8-(1H-imidazol-4-ylmethyl)-quinoline (Intermediate F2) was subjected to the appropriate process steps in Method A to produce 4-quinolin-8-ylmethyl-1,3-dihydro-imidazole-2-thione (Compound-8)

$^1$H NMR (300 MHz, methanol-d$^4$): δ 8.92 (dd, J=4.2, 1.8 Hz, 1H), 8.31 (dd, J=8.1, 1.5 Hz, 1H), 7.83 (dd, J=7.8, 1.2 Hz, 1H), 7.61-7.50 (series of m, 3H), 6.48 (s, 1H), 4.42 (s, 2H).

Example G

Method G: Procedure for the preparation of 4-quinolin-5-ylmethyl-1,3-dihydro-imidazole-2-thione (Compound 9)

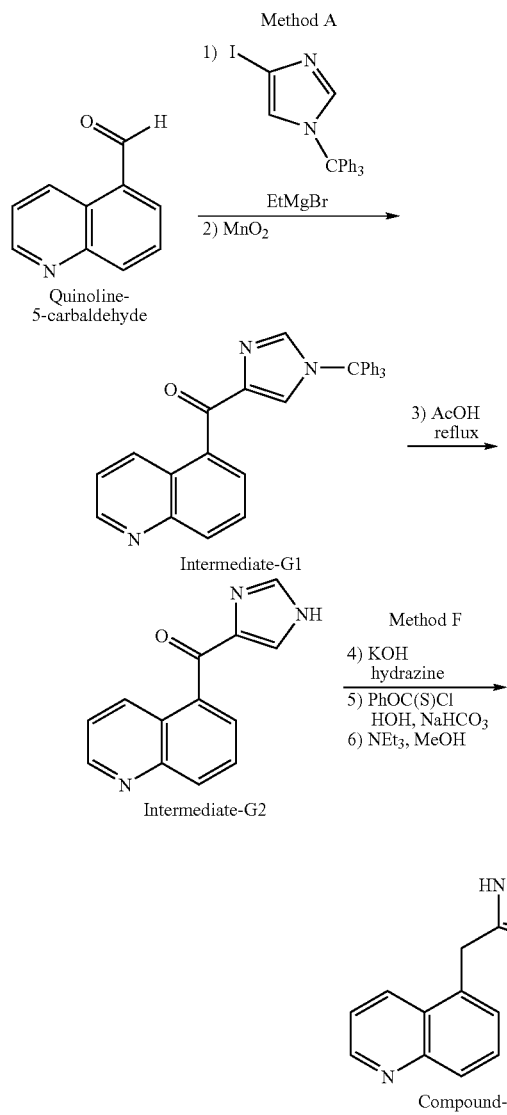

Quinoline-5-carbaldehyde (commercially available from Lancaster) was subjected to the applicable synthetic steps in Method A to produce quinolin-5-yl-(1-trityl-1H-imidazol-4-yl)-methanone (Intermediate G1).

Quinolin-5-yl-(1-trityl-1H-imidazol-4-yl)-methanone (Intermediate G1) in acetic acid:water (~2:1) was heated to 100° C. for 1 h. The mixture was basified with 1 M NaOH and extracted (6×) with $CHCl_3$: iPrOH (3:1). The organic solution was dried over $MgSO_4$, filtered, and concentrated onto silica gel. The material was eluted from a column of silica with 5% $NH_3$-MeOH: $CH_2Cl_2$ to give (1H-imidazol-4-yl)-quinolin-5-yl-methanone (Intermediate G2).

(1H-Imidazol-4-yl)-quinolin-5-yl-methanone (Intermediate G2) was subjected to the appropriate process steps in Method F to produce 4-quinolin-5-ylmethyl-1,3-dihydro-imidazole-2-thione (Compound-9)

$^1$H NMR (300 MHz, DMSO-d$^6$): δ 12.02 (brs, 1H), 11.71 (s, 1H), 8.88 (d, J=3.0 Hz, 1H), 8.55 (d, J=8.4 Hz, 1H), 7.91 (d, J=8.1 Hz, 1H), 7.69 (J=8.1 Hz, 1H), 7.56-7.46 (series of m, 2H), 6.50 (s, 1H), 4.18 (s, 2H).

Example H

Method H: Procedure for the Preparation of 4-(1-quinolin-8-yl-ethyl)-1,3-dihydro-imidazole-2-thione (Compound-10)

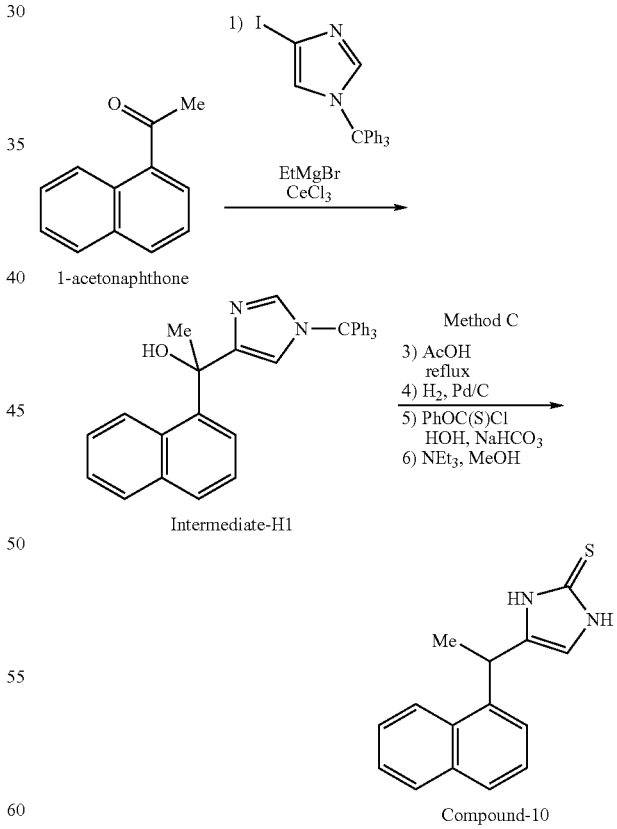

A mixture of 4-iodo-1-tritylimidazole (commercially available) (4.5 g, 10.3 mmol) in dichloromethane (50 mL) at 22° C. was treated with ethyl magnesium bromide (3.48 mL, 10.4 mmol, 3M in ether) and allowed to react for 1 h. Anhydrous $CeCl_3$ (3.3 g, 13.4 mmol) was added and the mixture was stirred for 30 m. A solution of 1-acetonaphthone (commercially available from Aldrich) (2.6 g, 15.9 mmol) in dichloromethane was added via syringe at 22° C. and stirred for 16 h. The mixture was quenched with a sat. solution of ammonium chloride (50 mL). The residue was isolated in a typical aqueous workup and purified by chromatography on silica gel with 50% EtOAc:hexane to give 1-naphthalen-1-yl-1-(1-trityl-1H-imidazol-4-yl)-ethanol (Intermediate H1) as a solid, 2.44 g (49%).

1-Naphthalen-1-yl-1-(1-trityl-1H-imidazol-4-yl)-ethanol (Intermediate H1) in acetic acid:water (~2:1) was heated to 100° C. for 1 h. The mixture was basified with 1 M NaOH and extracted (6×) with CHCl$_3$:iPrOH (3:1). The organic solution was dried over MgSO$_4$, filtered, and concentrated onto silica gel. The material was eluted from a column of silica with 5% NH$_3$-MeOH: CH$_2$Cl$_2$ to give 4-(1-naphthalen-1-yl-vinyl)-1H-imidazole.

4-(1-Naphthalen-1-yl-vinyl)-1H-imidazole was subjected to the appropriate process steps in Method C to produce 4-(1-naphthalen-1-yl-ethyl)-1,3-dihydro-imidazole-2-thione (Compound-10).

$^1$H NMR (300 MHz, DMSO-d$^6$ w/TMS): δ 11.90 (brs, 1H), 11.71 (brs, 1H), 8.16 (d, 7.8 Hz), 7.94-7.79 (m, 1H), 7.80 (d, J=8.1 Hz, 1H), 7.57-7.43 (m, 3H), 7.29 (dd, J=7.2, 1 Hz, 1H), 6.58 (s, 1H), 4.75 (q, J=7.2 Hz, 1H), 1.56 (d, J=6.9 Hz).

Example I

Method I: Procedure for the preparation of 4-naphthalen-2-ylmethyl-1,3-dihydro-imidazole-2-thione (Compound-11)

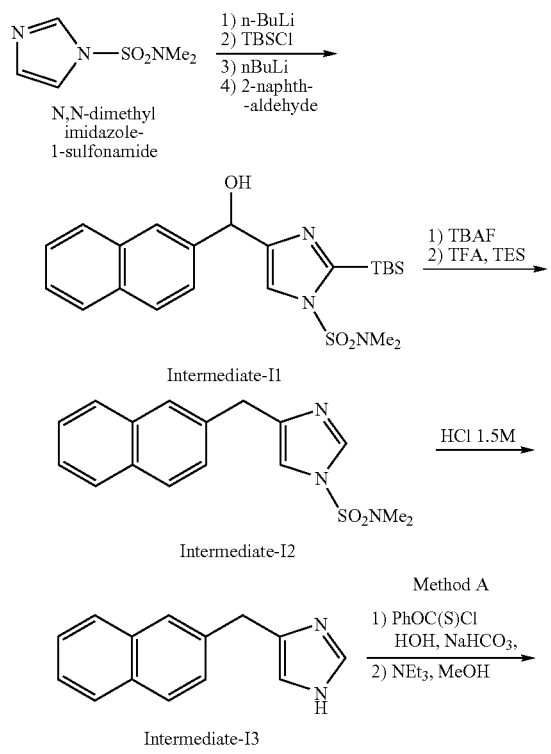

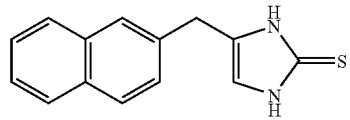
Compound-11

A solution of N,N-dimethyl imidazole-1-sulfonamide (commercially available from Aldrich) (2.0 g, 11.4 mmol) in THF (50 mL) at −78° C. was treated with nBuLi (4.6 mL of a 2.5 M soln) for 1 h. Solid tert-butyl-dimethylsilanyl chloride (TBSCl) (1.72 g, 11.4 mmol) in THF (10 mL) was added at rt for 16 h. The mixture was cooled to −20° C. and treated with nBuLi (4.6 mL of a 2.5 M soln) for 1 h. 2-Naphthaldehyde (1.78 g, 11.4 mmol) in THF (10 mL) was added and the mixture was stirred for 3 h at rt. The mixture was washed with brine and dried over Na$_2$SO$_4$. The solvent was removed under vacuum and the residue was purified by chromatography on silical gel with 25% EtOAc:hexane to give 2-(tert-butyl-dimethyl-silanyl)-4-(hydroxy-naphthalen-2-yl-methyl)-imidazole-1-sulfonic acid dimethylamide (Intermediate-I1) 2.6 g (50%).

2-(tert-Butyl-dimethyl-silanyl)-4-(hydroxy-naphthalen-2-yl-methyl)-imidazole-1-sulfonic acid dimethylamide (Intermediate-I1) (2.6 g, 5.4 mmol) in THF (30 mL) was treated with tetrabutylammonium fluoride (TBAF) (5.8 mL of a IM soln) at rt for 1 h. The reaction mixture was subjected to an aqueous work-up and the product was purified by chromatography on silica gel with 66% EtOAc:hexane to give 4-(hydroxy-naphthalen-2-yl-methyl)-imidazole-1-sulfonic acid dimethylamide as a white solid, 1.54 g (80%). 4-(Hydroxy-naphthalen-2-yl-methyl)-imidazole-1-sulfonic acid dimethylamide (1.0 g, 3.0 mmol) was deoxygenated with TES in TFA according to the applicable procedures outlined in Method A to give 4-naphthalen-2-yl-methyl-imidazole-1-sulfonic acid dimethylamide (Intermediate-I2) as a white solid 0.55 g, (58%).

A solution of 4-naphthalen-2-ylmethyl-imidazole-1-sulfonic acid dimethylamide (0.55 g, 1.7 mmol) in 1.5 M HCl (15 mL) was heated to reflux for 3 h. The mixture was cooled to rt and basified with NaOH solution. The mixture was extracted with ethyl acetate (2×) and the organic solution was dried over Na$_2$SO$_4$, filtered and evaporated to give 4-naphthalen-2-yl-methyl-1H-imidazole (Intermediate-I3) as a white solid 0.31 g (87%).

4-Naphthalen-2-yl-methyl-1H-imidazole (Intermediate-I3) was subjected to the appropriate process steps in Method A to produce 4-naphthalen-2-ylmethyl-1,3-dihydro-imidazole-2-thione (Compound 11).

$^1$H NMR (500 MHz, DMSO-d$^6$ w/TMS): δ 12.02 (s, 1H), 11.74 (s, 1H), 7.89-7.84 (m, 3H), 7.74 (s, 1H), 7.50-7.40 (m, 3H), 6.62 (s, 1H), 3.87 (s, 2H).

Example J

Method J: Procedure for the preparation of 4-[1-(2,3-dihydro-benzo[1,4]dioxin-6-yl)ethyl]-1,3-dihydro-imidazole-2-thione (Compound 12)

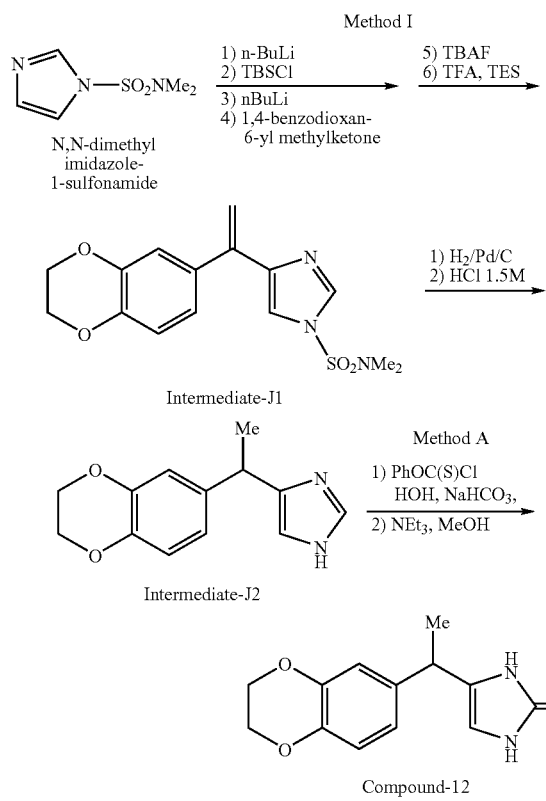

1,4-Benzodioxan-6-yl methyl ketone (commercially available from Aldrich) (1.56 g, 8.73 mmol a 10% excess) was subjected to the appropriate process steps in Method I to produce 4-[1-(2,3-dihydro-benzo[1,4]dioxin-6-yl)-vinyl]-imidazole-1-sulfonic acid dimethylamide (Intermediate-J1) as a white solid 0.64 g (24%).

4-[1-(2,3-Dihydro-benzo[1,4]dioxin-6-yl)-vinyl]-imidazole-1-sulfonic acid dimethylamide (Intermediate-J1) (0.25 g, 0.75 mmol) in EtOH (10 mL) was reduced with 10% Pd/C catalyst (25 mg) under 40 psi of hydrogen at rt for 2.5 h. The mixture was filtered through Celite. The solution was concentrated and the residue was dissolved in 1.5 M HCl (10 mL) and heated to reflux for 3 h. The mixture was cooled to rt and basified with sat solution of NaHCO₃. The mixture was extracted with ethyl acetate (2×) and the organic solution was dried over Na₂SO₄, filtered and evaporated to give 4-[1-(2,3-dihydro-benzo[1,4]dioxin-6-yl)-ethyl]-1H-imidazole (Intermediate-J2) as a tan solid 0.14 g (87%).

4-[1-(2,3-dihydro-benzo[1,4]dioxin-6-yl)-ethyl]-1H-imidazole (Intermediate-J2) was subjected to the appropriate process steps in Method A to produce 4-[1-(2,3-dihydro-benzo[1,4]dioxin-6-yl)-ethyl]-1,3-dihydro-imidazole-2-thione (Compound 12).

$^1$H NMR (300 MHz, CDCl₃ w/TMS): δ 10.9 (brs, 1H), 10.2 (brs, 1H), 6.78-6.68 (m, 3H), 6.40 (s, 1H), 4.24-4.22 (m, 5H), 1.50 (d, J=7.2 Hz, 3H).

Example K

Method K: Procedure for the Preparation of 4-thiochroman-6-ylmethyl-1,3-dihydro-imidazole-2-thione (Compound-13)

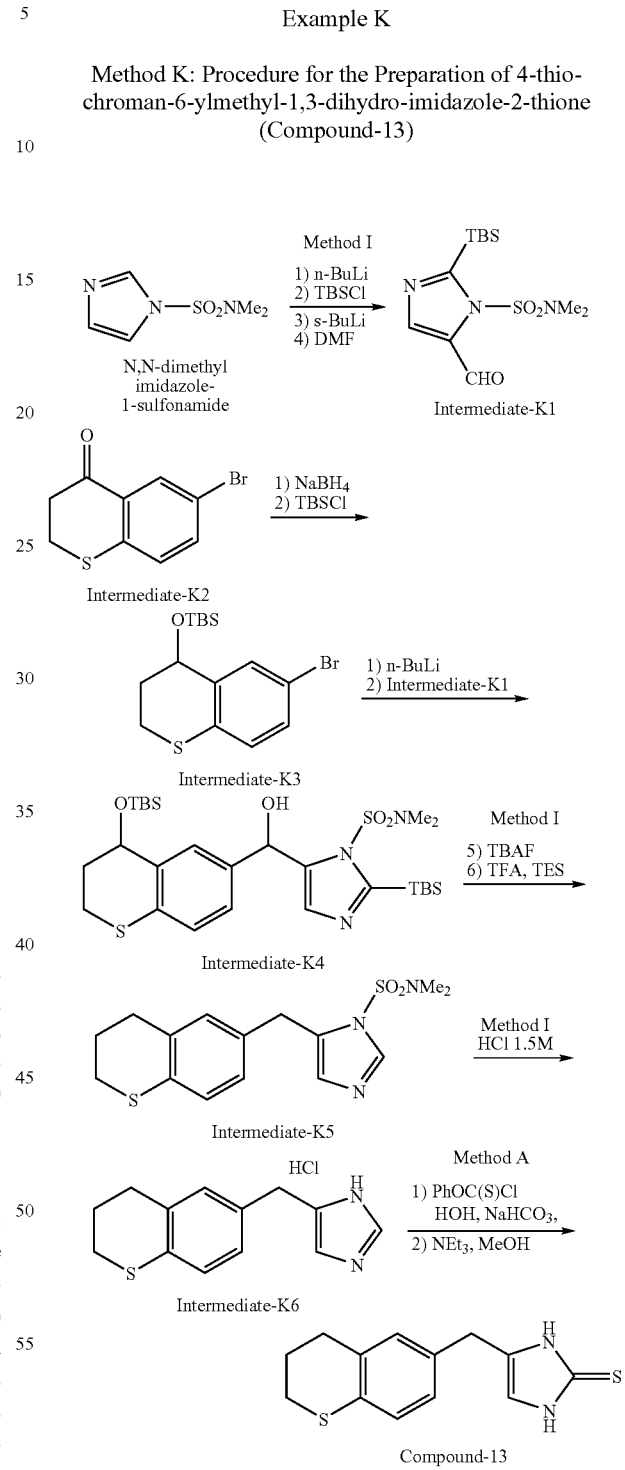

General Method for the formation of Intermediate K1: Dimethyl formamide and N,N-dimethyl imidazole-1-sulfonamide (commercially available from Aldrich) was subjected to the appropriate process steps in Method I to form 2-(tert-butyl-dimethyl-silanyl)-5-formyl-imidazole-1-sulfonic acid dimethylamide (Intermediate K1).

6-Bromo-thiochroman-4-one (Intermediate-K2) (prepared according to the procedures found in Johnson, A. T. et al Bioorg Med. Chem. 1999, 7, 1321. incorporated herein by reference) (1.11 g, 4.6 mmol) in MeOH (46 mL) was treated with sodium borohydride (0.14 g, 4.6 mmol) at 0° C. for 30 m. The mixture was subjected to a standard aqueous work-up and the alcohol, 6-bromo-thiochroman-4-ol, was used in the next step without further purification. 6-Bromo-thiochroman-4-ol (~4.5 mmol) in DMF (20 mL) was treated with imidazole (0.31 g) and TBSCl (0.69 g) at rt for 16 h. After an aqueous work-up the residue was purified by chromatography on silica gel with 10% EtOAc: hexanes to afford (6-bromo-thiochroman-4-yl-oxy)-tert-butyl-dimethyl-silane (Intermediate-K3) as a yellow oil, 1.06 g.

A solution of (6-bromo-thiochroman-4-yl-oxy)-tert-butyl-dimethyl-silane (Intermediate-K3) (2.74 g, 7.64 mmol) in THF (30 mL) was treated with nBuLi (3.1 mL of a 2.5 M soln) at −78° C. for 30 m. A solution of 2-(tert-butyl-dimethyl-silanyl)-5-formyl-imidazole-1-sulfonic acid dimethylamide (see the General Method above, Intermediate K1) (2.42 g, 7.63 mmol) in THF (10 mL) was added via cannula. After 15 m, the reaction mixture was allowed to warm to rt for 16 h. The mixture was quenched with water, washed with brine and dried over $Na_2SO_4$. The solvent was removed and the residue was purified by chromatography on silica gel with 20% EtOAc:hexane to afford 2-(tert-butyl-dimethyl-silanyl)-5-{[4-(tert-butyl-dimethyl-silanyloxy)-thiochroman-6-yl]-hydroxy-methyl}-imidazole-1-sulfonic acid dimethylamide (Intermediate K4) as an oil, 4.12 g.

2-(tert-Butyl-dimethyl-silanyl)-5-{[4-(tert-butyl-dimethyl-silanyloxy)-thiochroman-6-yl]-hydroxy-methyl}-imidazole-1-sulfonic acid dimethylamide (Intermediate K4) was subjected to the appropriate process steps in Method I and Method A to produce 4-thiochroman-6-ylmethyl-1,3-dihydro-imidazole-2-thione (Compound 13).

$^1$H NMR (500 MHz, DMSO-d$^6$ w/TMS): δ 11.93 (brs, 1H), 11.68 (s, 1H), 6.97 (d, J=7.5 Hz, 1H), 6.93 (s, 1H), 6.83 (d, J=7.5 Hz, 1H), 6.55 (s, 1H), 3.56 (s, 2H), 3.00-2.96 (m, 2H), 2.72-2.70 (m, 2H) 1.98-1.96 (m, 2H).

What is claimed is:

1. A compound of the formula

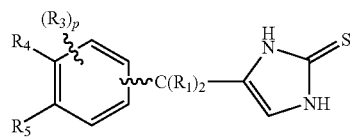

where $R_1$ is independently H, alkyl of 1 to 4 carbons, $CH_2OR_2$, or fluoro substituted alkyl of 1 to 4 carbons;

$R_2$ is independently H, alkyl of 1 to 4 carbons, $C(O)R_7$, carbocyclic aryl or heterocyclic aryl having 1 to 3 heteroatoms independently selected from N, O and S;

$R_3$ is independently selected from the groups consisting of alkyl of 1 to 4 carbons, alkenyl of 2 to 4 carbons, alkynyl of 2 to 4 carbons, $CH_2OR_2$, $CH_2N(R_2)_2CH_2CN$, $C(O)R_2$, $C(O)OR_6$, $SO_3R_6$, $SO_2N(R_2)_2CH_2SR_2$, F, Cl, Br, I, fluoro substituted alkyl of 1 to 4 carbons, CN, $N_3$, $NO_2$, $N(R_2)_2$, $OR_2$, $SR_2$;

p is an integer having the values of 0, 1, 2, or 3;

$R_4$ and $R_5$ together with the carbons to which they are attached jointly form a carbocyclic or a heterocyclic ring, the heterocyclic ring having 5 or 6 atoms in the ring and 1 to 3 heteroatoms independently selected from N, O and S;

said carbocyclic or heterocyclic ring jointly formed by $R_4$ and $R_5$ being optionally substituted with 1 to 7 $R_8$ groups;

$R_6$ is independently H, alkyl of 1 to 4 carbons, carbocyclic aryl or heterocyclic aryl having 1 to 3 heteroatoms independently selected from N, O and S;

$R_7$ is H or alkyl of 1 to 4 carbons, and $R_8$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)R_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, $SR_2$ or $R_8$ is O or S double bonded to one carbon of said carbocyclic or heterocyclic ring.

2. The compound according to claim 1 which is used for the treatment of a condition selected from the group consisting of hypertension, depression, glaucoma, elevated intraocular pressure, ischemic neuropathies, optic neuropathy, corneal pain, headache pain, migraine, cancer pain, back pain, muscle pain, fibromyalgia, pain associated with diabetic neuropathy, the treatment of diabetic retinopathy, stroke, drug dependence, withdrawal symptoms, obsessive compulsive disorder, obesity, insulin resistance, diarrhea, nasal congestions, spasticity, and attention deficit disorder.

3. The compound according to claim 1 wherein the compound is administered to a human patient in the range of about 1-1000 mg/day.

4. The compound according to claim 3 wherein the compound is administered to a human patient in the range of about 10 to about 500 mg/day.

5. The compound according to claim 3 wherein the compound may be administered to a patient by one of the routes selected from the group consisting of transdermal, parenteral, subcutaneous, intranasal, intrathecal, intramuscular, and intravenous.

* * * * *